(12) United States Patent
Ellingson et al.

(10) Patent No.: US 9,958,515 B2
(45) Date of Patent: May 1, 2018

(54) CONFIGURING OPERATING PARAMETERS OF A MEDICAL DEVICE BASED ON A TYPE OF SOURCE OF A DISRUPTIVE ENERGY FIELD

(75) Inventors: Michael L. Ellingson, St. Louis Park, MN (US); Hyun J. Yoon, Vadnais Heights, MN (US); Piotr J. Przybyszewski, Coon Rapids, MN (US); Patrick L. Parish, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 2225 days.

(21) Appl. No.: 12/648,547

(22) Filed: Dec. 29, 2009

(65) Prior Publication Data

US 2011/0106212 A1    May 5, 2011

Related U.S. Application Data

(60) Provisional application No. 61/256,342, filed on Oct. 30, 2009.

(51) Int. Cl.
*A61N 1/00* (2006.01)
*G01R 33/28* (2006.01)
*A61N 1/37* (2006.01)

(52) U.S. Cl.
CPC ......... *G01R 33/288* (2013.01); *A61N 1/3718* (2013.01)

(58) Field of Classification Search
CPC ............................ A61N 1/3718; G01R 33/288
USPC .................................. 607/9, 27, 28
See application file for complete search history.

(56) References Cited

U.S. PATENT DOCUMENTS

| | | | |
|---|---|---|---|
| 4,091,818 A * | 5/1978 | Brownlee et al. | 607/9 |
| 6,937,906 B2 | 8/2005 | Terry et al. | |
| 7,164,950 B2 | 1/2007 | Kroll et al. | |
| 7,212,863 B2 | 5/2007 | Strandberg | |
| 7,369,898 B1 | 5/2008 | Kroll et al. | |
| 2003/0144705 A1* | 7/2003 | Funke | 607/27 |
| 2004/0088012 A1* | 5/2004 | Kroll et al. | 607/9 |
| 2004/0263172 A1 | 12/2004 | Gray et al. | |
| 2007/0021814 A1* | 1/2007 | Inman et al. | 607/141 |

(Continued)

FOREIGN PATENT DOCUMENTS

| | | |
|---|---|---|
| EP | 1493460 A1 | 5/2005 |
| WO | 2010/062978 A2 | 6/2010 |

OTHER PUBLICATIONS (PCT/US2010/031214) PCT Notification of Transmittal of the International Search Report and the Written Opinion of the International Searching Authority, 11 pages.

*Primary Examiner* — Lindsey G Wehrheim

(57) ABSTRACT

An implantable medical device (IMD) configures one or more operating parameters of the IMD based on a type of source of a disruptive energy field to which the IMD is exposed. The disruptive energy field may, in one example, include magnetic and/or radio frequency (RF) fields generated by an MRI scanner. In one aspect, the IMD may distinguish between different types of MRI scanners and select an exposure operating mode tailored to reduce the effects of the particular type of MRI scanner. In another aspect, the IMD may adjust one or more operating parameters that will be used when the IMD returns to a normal operating mode after exposure to the MRI scanner based on the type of MRI scanner to which the IMD is exposed.

28 Claims, 9 Drawing Sheets

(56) References Cited

U.S. PATENT DOCUMENTS

| | | |
|---|---|---|
| 2007/0173910 A1 | 7/2007 | Armstrong |
| 2008/0065181 A1* | 3/2008 | Stevenson .................... 607/115 |
| 2008/0082146 A1 | 4/2008 | Gandhi et al. |
| 2009/0157146 A1 | 6/2009 | Linder et al. |
| 2009/0210025 A1 | 8/2009 | Ameri |
| 2009/0306735 A1 | 12/2009 | Lagercrantz et al. |

* cited by examiner

US 9,958,515 B2

CONFIGURING OPERATING PARAMETERS OF A MEDICAL DEVICE BASED ON A TYPE OF SOURCE OF A DISRUPTIVE ENERGY FIELD

This application claims priority from U.S. Provisional Application No. 61/256,342, filed Oct. 30, 2009, the entire content of which is incorporated herein by reference.

TECHNICAL FIELD

The disclosure relates generally to implantable medical devices and, in particular, to the configuration of operating parameters of an implantable medical device (IMD) based on a type of source of a disruptive energy field to which the IMD is exposed.

BACKGROUND

A wide variety of IMDs that deliver a therapy to and/or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in undesirable operation of the IMD. The IMD may be exposed to the disruptive energy field for any of a number of reasons. For example, one or more medical procedures may need to be performed on the patient within whom the IMD is implanted for purposes of diagnostics or therapy. For example, the patient may need to have a magnetic resonance imaging (MRI) scan, computed tomography (CT) scan, electrocautery, diathermy or other medical procedure that produces a magnetic field, electromagnetic field, electric field or other disruptive energy field.

The disruptive energy field may induce energy on one or more of the implantable leads coupled to the IMD or directly on one or more components of the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads or on the components of the IMD may result in inadvertent stimulation or heating of the tissue and/or nerve site adjacent to the electrodes of the leads or adjacent to the housing of the IMD. Such heating may compromise pacing and sensing thresholds at the site, which could result in reduced therapy efficacy.

SUMMARY

In general, this disclosure relates to configuration of operating parameters of an implantable medical device (IMD) based on a type of source of a disruptive energy field to which the IMD is exposed. The disruptive energy field may, in one example, include magnetic and/or radio frequency (RF) fields generated by an MRI scanner. Although the techniques of this disclosure are described in the context of disruptive energy fields generated by an MRI scanner, the techniques may be used to control operation of the IMD within environments in which other types of disruptive energy fields of other sources are present.

The IMD is configured into an exposure operating mode prior to or upon exposure to the disruptive energy field. The exposure operating mode causes the IMD to operate in a manner that accounts for the presence of strong disruptive energy fields. In accordance with the techniques of this disclosure, the IMD may distinguish different types of disruptive field sources based on one or more detected conditions and configure operating parameters of the IMD based on the type of disruptive field source detected. In one aspect, the IMD may distinguish between different types of MRI scanners and select a first exposure operating mode for a first type of MRI scanner (e.g., a 1.5 Tesla (1.5 T) MRI scanner) and select a second exposure operating mode for a second type of MRI scanner (e.g., a 3.0 Tesla (3.0 T) MRI scanner). The operating parameters of each of the exposure operating modes may be tailored to reduce the effects of the different MRI scanners, which produce different magnetic fields and RF field frequencies.

In another aspect, the IMD may adjust one or more operating parameters that will be used when the IMD returns to a normal operating mode based on the type of disruptive field source. For example, the IMD may adjust the one or more operating parameters of the normal operating mode by a first amount when exposed to a first type of MRI scanner (e.g., a 1.5 T MRI scanner) and adjust the one or more operating parameters by a second amount when exposed to a second type of MRI scanner (e.g., a 3.0 T MRI scanner). The one or more parameters of the normal operating mode that are adjusted based on the type of MRI scanner may include a pacing amplitude, a pacing pulse width, and/or a sensitivity of a sense amplifier. The adjustment of the one or more parameters for use in the normal operating mode after exposure to the MRI scanner may be in addition to or instead of selecting different exposure operating modes.

In one example, this disclosure is directed to an implantable medical device comprising a memory to store operating parameters for a plurality of exposure operating modes, wherein each of the plurality of exposure operating modes corresponds to a particular type of magnetic resonance imaging (MRI) scanner, and a processor to detect a condition indicative of a presence of an MRI scanner, determine a type of MRI scanner in response to detecting the condition, retrieve from the memory the operating parameters of the one of the plurality of exposure operating modes corresponding to the determined type of MRI scanner, and configure the implantable medical device to operate in accordance with the retrieved operating parameters.

In another example, this disclosure is directed to a method comprising detecting a condition indicative of a presence of a magnetic resonance imaging (MRI) scanner, determining a type of MRI scanner in response to detecting the condition, selecting one of a plurality of exposure operating modes based on the determination of the type of MRI scanner, wherein each of the plurality of exposure operating modes corresponds to operating parameters for use during exposure to a particular type of MRI scanner, and configuring the implantable medical device to operate in accordance with the operating parameters of the selected exposure operating mode.

In a further example, this disclosure is directed to an implantable medical device comprising means for storing a plurality of exposure operating modes, wherein each of the plurality of exposure operating modes corresponds to operating parameters for use during exposure to a particular type of a magnetic resonance imaging (MRI) scanner, means for detecting a condition indicative of a presence of MRI scanner, means for determining a type of MRI scanner in response to detecting the condition, means for selecting one of the plurality of exposure operating modes based on the determination of the type of MRI scanner, and means for configuring the implantable medical device to operate in accordance with the operating parameters of the selected exposure operating mode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
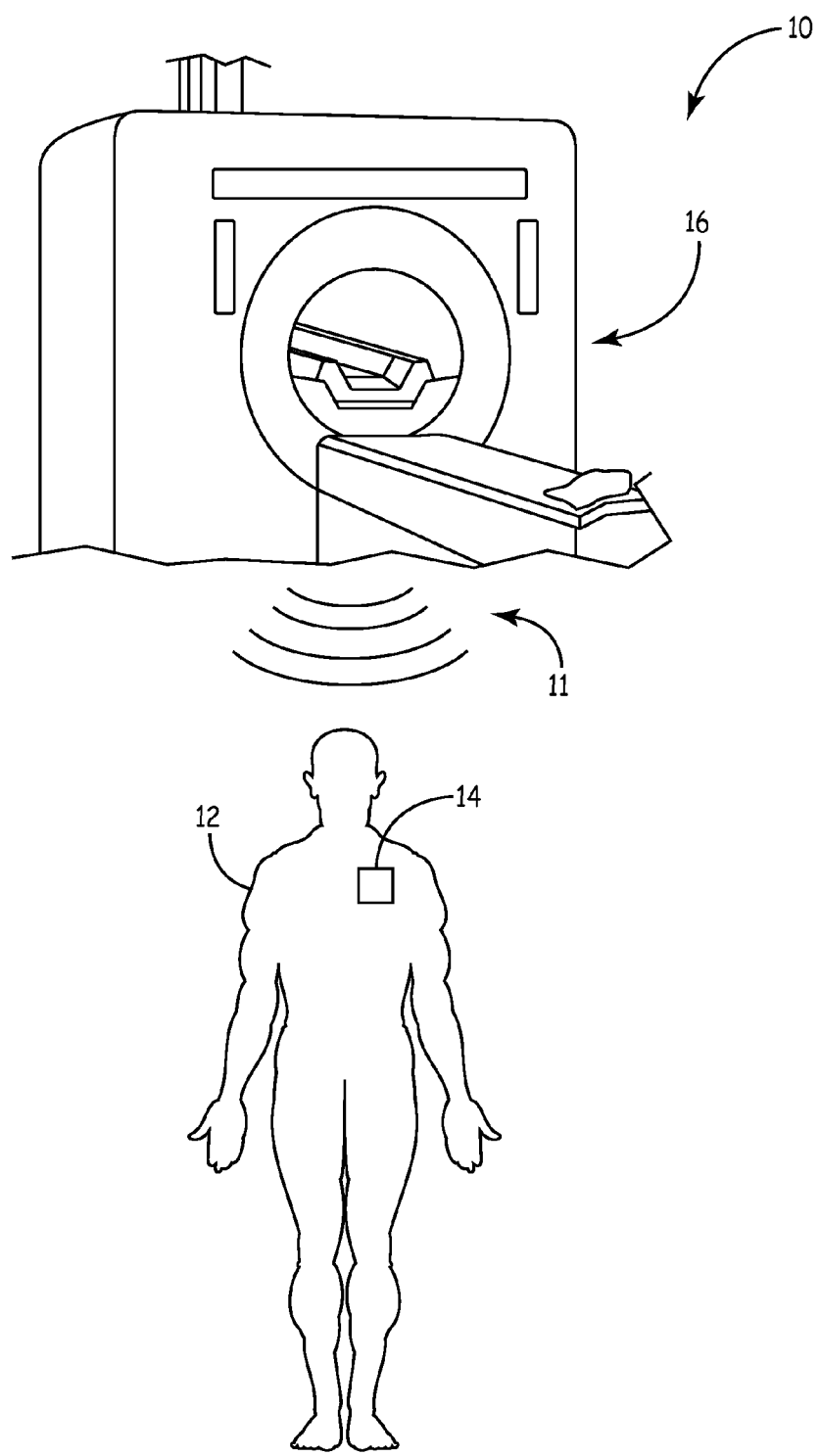
FIG. 1 is a conceptual diagram illustrating an environment in which an implantable medical device (IMD) is exposed to a disruptive energy field.

FIG. 1 is a conceptual diagram illustrating an environment 10 in which an implantable medical device (IMD) 14 is exposed to a disruptive energy field 11. IMD 14 is implanted within patient 12 to provide therapy to and/or to monitor a physiological condition of patient 12. The techniques, however, are not limited to devices implanted within patient 12. For example, the techniques may be used in conjunction with an external medical device that is adversely affected by disruptive energy field 11.

IMD 14 may be any of a variety of devices that provide therapy to patient 12, monitor a condition of patient 12, or both. For example, IMD 14 may be a device that provides electrical stimulation therapy via one or more implantable leads that include one or more electrodes (not shown in FIG. 1). In some instances, IMD 14 may be a device that provides electrical stimulation therapy in the form of cardiac rhythm management therapy to a heart of patient 12 via leads implanted within one or more atria and/or ventricles of the heart. In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarizatoin of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like. In some instances, IMD 14 may be used solely for monitoring a condition of patient 12. In other words, IMD 14 may not provide therapy to patient 12, but simply sense a physiological or biological condition of patient 12.

In yet other instances, IMD 14 may be a device that delivers a drug or therapeutic agent to patient 12, e.g., via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 10 includes an energy source or disruptive field source that generates disruptive energy field 11 to which IMD 14 is exposed. In the example illustrated in FIG. 1, the energy source or disruptive field source is an MRI scanner 16. Although the techniques of this disclosure are described with respect to disruptive energy field 11 generated by MRI scanner 16, the techniques may be used to control operation of IMD 14 within environments in which other types of disruptive energy fields are present. For example, IMD 14 may operate in accordance with the techniques of this disclosure in environments in which disruptive energy field 11 is generated by other sources, such as a CT scanner, X-ray machine, electrocautery device, diathermy device, ablation device, radiation therapy device, electrical therapy device, magnetic therapy device, RFID security gate, or any other environment with devices that radiate energy to produce magnetic, electromagnetic, electric fields or other disruptive energy fields.

MRI scanner 16 uses magnetic and radio frequency (RF) fields to produce images of body structures for diagnosing injuries, diseases and/or disorders. In particular, MRI scanner 16 generates a static magnetic field, gradient magnetic fields and/or RF fields. The static magnetic field is a non-varying magnetic field that is typically always present around MRI scanner 16 whether or not an MRI scan is in progress. Gradient magnetic fields are pulsed magnetic fields that are typically only present while the MRI scan is in progress. RF fields are pulsed RF fields that are also typically only present while the MRI scan is in progress. The magnitude, frequency or other characteristic of disruptive energy field 11 may vary based on the type of MRI scanner producing the field.

Some or all of the various types of fields produced by MRI scanner 16 may interfere with operation of IMD 14. In other words, one or more of the various types of fields produced by MRI scanner 16 may make up disruptive energy field 11. For example, the gradient magnetic and RF fields produced by MRI scanner 16 may induce energy on one or more of the implantable leads coupled to IMD 14. In some instances, IMD 14 inappropriately detects the induced energy on the leads as physiological signals, which may in turn cause IMD 14 to deliver undesired therapy or withhold desired therapy. In other instances, the induced energy on the leads result in IMD 14 not detecting physiological signals that are actually present, which may again result in IMD 14 delivering undesired therapy or withholding desired therapy. The induced energy on the leads or on the components of IMD 14 may be delivered to the tissue of patient 12 resulting in inadvertent stimulation or heating of the tissue adjacent to electrodes of the leads or adjacent to the housing of IMD 14. Such heating may compromise pacing and sensing thresholds at the site, which could result in reduced therapy efficacy.

To reduce the undesirable effects of disruptive energy field 11, IMD 14 is capable of operating in accordance with settings that are less susceptible to undesirable operation during exposure to disruptive energy field 11, referred to herein as the "exposure mode" or "exposure operating mode." In the case of an exposure operating mode that specifically accounts for MRI scans, the mode may be referred to as an MR Conditional mode or an MR Safe mode. Prior to being exposed or upon being exposed to disruptive energy field 11, IMD 14 is configured from a normal operating mode (e.g., the current operating mode) to the exposure operating mode. IMD 14 may be automatically configured into the exposure operating mode in response to detecting one or more conditions indicative of the presence of MRI scanner 16.

As will be described in more detail below, IMD 14 may determine the type of MRI scanner 16 to which IMD 14 is being exposed and adjust one or more operating parameters of IMD 14 based on the type of MRI scanner 16. IMD 14 may, for example, determine the type of MRI scanner 16 based on one or more of a magnitude of a static and/or gradient magnetic field or a frequency of an RF field applied by the MRI scanner 16. In one aspect of this disclosure, IMD 14 may select an exposure operating mode that is specifically tailored for the type of MRI scanner 16. In this manner, the exposure operating mode may be specifically tailored to reduce the effects of the magnetic and RF fields of different magnitudes and/or frequencies that correspond to the type of MRI scanner. In another aspect of this disclosure, IMD 14 may adjust one or more operating parameters that will be used when IMD 14 returns to the normal operating mode based on the type of MRI scanner 16. In this manner, IMD 14 may adjust therapy or sensing to account for any effects caused by exposure to MRI scanner 16.

Figure 2:
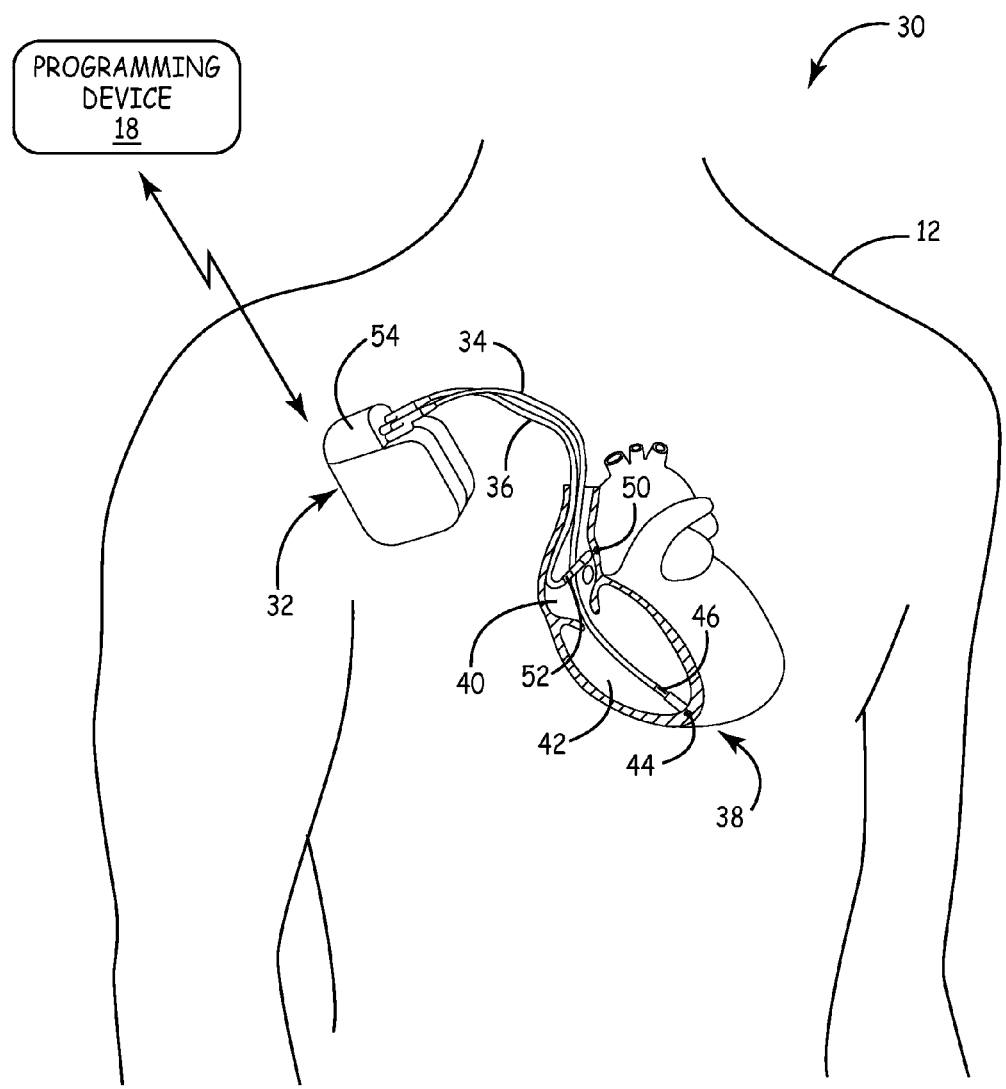
FIG. 2 is a conceptual diagram illustrating an example medical system that may be used to provide therapy to patient.

FIG. 2 is a conceptual diagram illustrating an example medical system 30 that may be used to provide therapy to patient 12. Medical system 30 includes an IMD 32 and leads 34 and 36 that extend from IMD 32. IMD 32 may, for example, correspond to IMD 14 of FIG. 1. IMD 32 wirelessly communicates with programming device 18.

In the example illustrated in FIG. 2, IMD 32 is an implantable cardiac device that senses electrical activity of a heart 38 of patient 12 and/or provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT). The combinations of cardiac therapies provided may be dependent on a condition of patient 12. In some instances, IMD 32 may provide no therapy to patient 12, but instead provide only sensing of electrical activity or other variable of heart 38, such as in the case of an implantable loop recorder.

In the illustrated example, lead 34 is a right ventricular (RV) lead that extends through one or more veins (not shown), the superior vena cava (not shown), and right atrium 40, and into right ventricle 42 of heart 38. Lead 34 includes electrodes 44 and 46 located along a distal end of lead 34. In the illustrated example, lead 36 is right atrial (RA) lead that extends through one or more veins and the superior vena cava, and into the right atrium 40 of heart 38. Lead 36 includes electrodes 50 and 52 located along a distal end of lead 36.

Electrodes 44 and 50 may take the form of extendable helix tip electrodes mounted retractably within an insulative electrode head (not shown) of respective leads 34 and 36. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated lead 34 or 36. Additionally, either or both of leads 34 and 36 may include more than two electrodes or only a single electrode.

Each of the electrodes 44, 46, 50 and 52 may be electrically coupled to a respective conductor within the body of its associated lead 34 and 36. The respective conductors may extend from the distal end of the lead to the proximal end of the lead and couple to circuitry of IMD 32. For example, leads 34 and 36 may be electrically coupled to a stimulation module, a sensing module, or other modules of IMD 32 via connector block 54. In some examples, proximal ends of leads 34 and 36 may include electrical contacts that electrically couple to respective electrical contacts within connector block 54. In addition, in some examples, leads 34 and 36 may be mechanically coupled to connector block 54 with the aid of set screws, connection pins or another suitable mechanical coupling mechanism.

When IMD 32 is capable of delivering electrical stimulation therapy, IMD 32 delivers the therapy (e.g., pacing pulses) to heart 38 via any combination of electrodes 44, 46, 50 and 52 to cause depolarization of cardiac tissue of heart 38. For example, IMD 32 may deliver bipolar pacing pulses to right atrium 40 via electrodes 50 and 52 of lead 36 and/or may deliver bipolar pacing pulses to right ventricle 42 via electrodes 44 and 46 of lead 34. In another example, IMD 32 may deliver unipolar pacing pulses to atrium 40 and ventricle 42 using a housing electrode (not shown) in conjunction with one of electrodes 44, 46, 50 and 52. The housing electrode may be formed integrally with an outer surface of the hermetically-sealed housing of IMD 32 or otherwise coupled to the housing. In some examples, the housing electrode is defined by an uninsulated portion of an outward facing portion of the housing of IMD 32.

Electrodes 44, 46, 50 and 52 may also sense electrical signals attendant to the depolarization and repolarization of heart 38. The electrical signals are conducted to IMD 32 via one or more conductors of respective leads 34 and 36. IMD 32 may use any combinations of the electrodes 44, 46, 50, 52 or the housing electrode for unipolar or bipolar sensing. As such, the configurations of electrodes used by IMD 32 for sensing and pacing may be unipolar or bipolar depending on the application. IMD 32 may analyze the sensed signals to monitor a rhythm of heart 38 or detect an arrhythmia of heart 38, e.g., tachycardia, bradycardia, fibrillation or the like. In some instances, IMD 32 provides pacing pulses (or other therapy) to heart 38 based on the cardiac signals sensed within heart 38. In other words, pacing may be responsive to the sensed events.

As described above, exposure of IMD 32 to a disruptive energy field 11 (FIG. 1) may result in undesirable operation. For example, gradient magnetic and RF fields produced by MRI scanner 16 (FIG. 1) may induce energy on one or more conductors of respective ones of implantable leads 34 and 36 or on the housing electrode. In some instances, IMD 32 inappropriately detects the induced energy on the conductors of leads 34 or 36 as physiological signals, which may in turn cause IMD 32 to deliver undesired therapy or withhold desired therapy. In other instances, the induced energy on the conductors of leads 34 or 36 result in IMD 32 not detecting physiological signals that are actually present, which may again result in IMD 32 delivering undesired therapy or withholding desired therapy. In further instances, the induced energy on conductors of leads 34 or 36 or on components of IMD 32 results in inadvertent stimulation or heating of the tissue adjacent to electrodes 44, 46, 50 and 52 or the housing of IMD 32. Such heating may compromise pacing and sensing thresholds at the site, which could result in reduced therapy efficacy.

Configuring IMD 32 into an exposure operating mode may reduce, and possibly eliminate, the undesirable effects that may be caused by exposure to disruptive energy field 11. As such, IMD 32 may be configured to operate in the exposure operating mode prior to or immediately subsequent to entering the environment 10 in which the disruptive energy field 11 is present, or prior to or immediately subsequent to the beginning of an MRI scan. In accordance with one aspect of this disclosure, IMD 32 detects a condition indicative of a presence of an MRI scanner and determines a type of MRI scanner in response to detecting the condition. As will be described in further detail below, IMD 32 may determine the type of MRI scanner based on the detected condition, based on one or more other conditions or based on the detected condition and one or more other conditions.

Based on the determination of the type of MRI scanner, IMD 32 adjusts one or more operating parameters of IMD 32. For example, IMD 32 may select the exposure operating mode corresponding to the particular type of MRI scanner. In another example, IMD 32 may adjust one or more operating parameters to be used in the normal operating mode upon no longer being exposed based on the type of MRI scanner.

A user, such as a physician, may interact with programming device 18 to configure one or more parameters of the plurality of exposure operating modes. For example, the user may specify a pacing mode (e.g., atrial-based pacing mode, ventricular-based pacing mode or dual-chamber based pacing mode), pacing amplitude, pacing pulse width, and/or pacing rate of the therapy energy delivered during the exposure operating mode. Typically, the pacing mode, pacing amplitude, pacing pulse width, and pacing rate of the therapy energy delivered during the exposure operating mode will be the same regardless of the type of MRI scanner. However, in some instances, one or more of these settings may be different based on the type of MRI scanner 16.

As another example, the user may specify filtering configurations to be used during each of the exposure operating modes. The user may, for example, configure the exposure operating mode corresponding to a 1.5 T MRI scanner to implement a filter to attenuate signals at a first frequency (e.g., 64 MHz) and configure the exposure operating mode corresponding to a 3.0 T MRI scanner to implement a filter to attenuate signals at a second frequency (e.g., 128 MHz). Programming device 18 then transmits the selected settings of the one or more exposure operating modes to IMD 32.

As a further example, the user may interact with programming device 18 to configure one or more parameters for use in the normal operating mode after being exposed to the MRI scanner. In some instances, these parameters may differ based on the type of MRI scanner to which IMD 32 is exposed. For example, the user may specify pacing parameters and/or sensing parameters to use during the normal operating mode after the exposure to MRI scanner 16 that may be different due to different MRI-induced effects that may occur based on the type of MRI scanner 16.

The user may interact with a programming device 18 to communicate with IMD 32 for other purposes than configuring the exposure operating mode parameters. For example, the user may interact with programming device 18 to retrieve physiological information, diagnostic information, logs of delivered therapies, or an assessment of the performance or integrity of IMD 32 or other components of medical system 30, such as leads or a power source of IMD 32. Programming device 18 may transmit a communication requesting such information or receive the information without providing such a request. The user may also interact with programming device 18 to program IMD 32, e.g., select values for operational parameters of the normal operating mode of IMD 32, such as a therapy progression, an electrode or combination of electrodes of leads 34 and 36 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like.

Programming device 18 may communicate with IMD 32 via wireless communication using any techniques known in the art. Examples of communication techniques may include, for example, magnetic telemetry, low frequency telemetry, RF telemetry, tissue conductance telemetry (in which the body is used as a conductor), or acoustic telemetry, but other techniques are also contemplated. In some instances, programming device 18 and IMD 32 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

Programming device 18 may be a dedicated hardware device with dedicated software for programming of IMD 32. Alternatively, programming device 18 may be an off-theshelf computing device running an application that enables programming device 18 to program IMD 32. In some examples, programming device 18 may be a handheld computing device or a computer workstation. Programming device 18 may, in some instances, include a programming head that may be placed proximate to the patient's body near the implant site of IMD 32 in order to improve the quality or security of communication between IMD 32 and programming device 18. Programming device 18 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

The configuration of medical system 30 illustrated in FIG. 2 is merely an example. In other examples, medical system 30 may include more or fewer leads extending from IMD 32. For example, IMD 32 may be coupled to three leads, e.g., a third lead implanted within a left ventricle of heart 30. In another example, IMD 32 may be coupled to a single lead that is implanted within either an atrium or ventricle of heart 38. As such, IMD 32 may be used for single chamber or multi-chamber cardiac rhythm management therapy.

In addition to more or fewer leads, each of the leads may include more or fewer electrodes. In instances in which IMD 32 is used for therapy other than pacing, e.g., defibrillation or cardioversion, the leads may include elongated electrodes, which may, in some instances, take the form of a coil. IMD 32 may deliver defibrillation or cardioversion shocks to heart 38 via any combination of the elongated electrodes and housing electrode. As another example, medical system 30 may include leads with a plurality of ring electrodes, e.g., as used in some implantable neurostimulators.

In still other examples, a medical system may include epicardial leads and/or patch electrodes instead of or in addition to the transvenous leads 34 and 36 illustrated in FIG. 2. Further, IMD 32 need not be implanted within patient 12. In examples in which IMD 32 is not implanted in patient 12, IMD 32 may deliver electrical stimulation therapy to heart 38 via percutaneous leads that extend through the skin of patient 12 to a variety of positions within or outside of heart 38.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
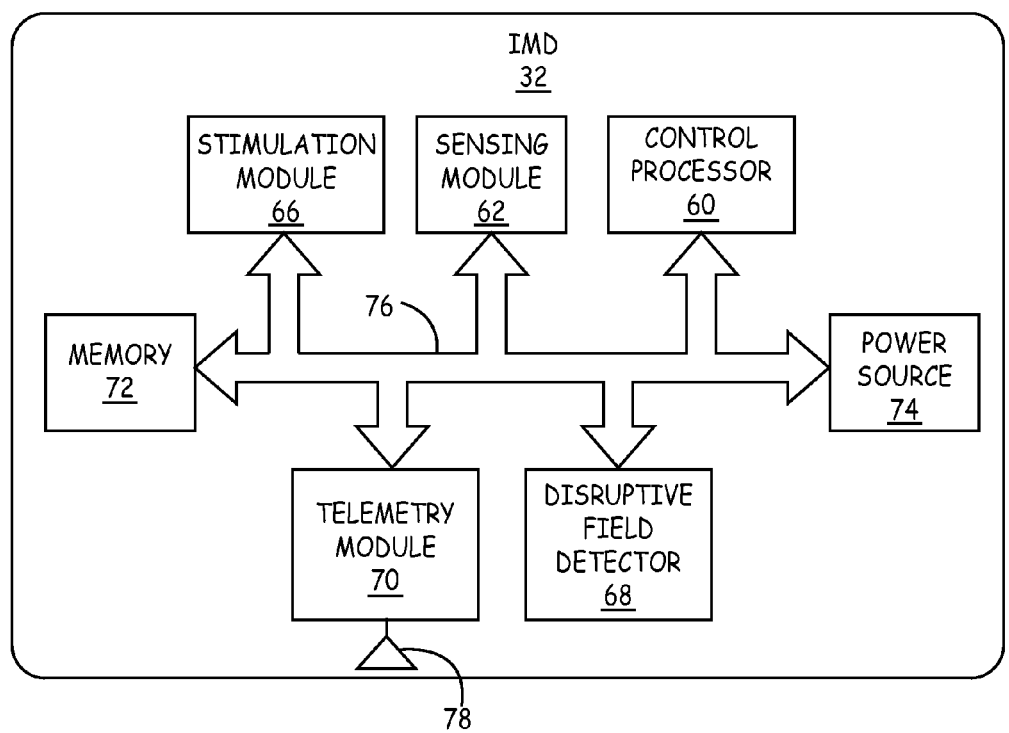
FIG. 3 is a functional block diagram of an example configuration of components of an IMD.

FIG. 3 is a functional block diagram of an example configuration of components of IMD 32. In the example illustrated by FIG. 3, IMD 32 includes a control processor 60, sensing module 62, stimulation module 66, disruptive field detector 68, telemetry module 70, memory 72 and power source 74, all of which are interconnected by a data bus 76.

As described above, IMD 32 may detect a condition indicative of a presence of MRI scanner 16 and determine a type of MRI scanner in response to detecting the condition.

Processor 60 of IMD 32 may receive a signal from disruptive field detector 68 and analyze the signal from disruptive field detector 68 to detect the condition indicative of the presence of MRI scanner 16. In one example, disruptive field detector 68 is a magnetic field detector that provides an output that varies as a function of the magnitude of the magnetic field. Processor 60 may analyze the output of disruptive field detector 68 to determine the whether the condition indicative of the presence of MRI scanner 16 exists. In the case of the magnetic field detector, for example, processor 60 may determine whether the magnitude of the magnetic field exceeds a threshold.

In response to detecting the presence of MRI scanner 16, processor 60 may determine the type of MRI scanner. Processor 60 may determine the type of MRI scanner based on the signals used to detect the presence of MRI scanner 16, based on one or more other signals or based on the signals used to detect the presence of MRI scanner 16 and one or more other conditions. For example, processor 60 may determine the type of MRI scanner based on the signals from the magnetic field detector of disruptive field detector 68. Processor 60 may analyze these signals to determine whether the magnitude corresponds with a 1.5 T MRI scanner or a 3.0 T MRI scanner. In instances in which the same signals are used to detect the presence and type of MRI scanner 16, processor 60 may be viewed as concurrently detecting the presence and type of MRI scanner 16.

In another example, processor 60 determines the type of MRI scanner based on at least one other signal. For instance, upon detecting the condition indicative of the presence of the MRI scanner (e.g., magnitude of magnetic field exceeds a threshold), processor 60 may determine a frequency of RF energy to determine the type of MRI scanner. Processor 60 may determine that the MRI scanner is a 1.5 T scanner when the frequency of RF energy is approximately 64 MHz and determine that the MRI scanner is a 3.0 T MRI scanner when the frequency of the RF energy is approximately 128 MHz. To this end, disruptive field detector 68 may include an RF sensor comprising a stub, coil, or other structure that operates as an antenna to receive RF energy. In another example, a signal may be induced on antenna 78 by the pulsed RF fields generated by MRI scanner 16. In a further example, a signal may be induced on one or more conductors within leads 34 or 36 by the pulsed RF fields generated by MRI scanner 16.

In any case, processor 60 may analyze signals induced on disruptive field detector 68, antenna 78 and/or conductors of leads 34 and 36 to determine the frequency of the RF energy. Based on the frequency of the RF energy, processor 60 may determine the type of MRI scanner. In this example, processor 60 detects the presence of MRI scanner 16 in response to detecting a first condition, e.g., the detection of a strong magnetic field, and determines the type of MRI scanner based on a second condition, e.g., the determined frequency of RF energy. Other techniques may be used to determine the presence of MRI scanner 16 and/or the type of MRI scanner using any of a variety of conditions. The examples above are for example purposes only and should not be considered limiting of the techniques described in this disclosure.

Processor 60 may select an exposure operating mode corresponding to the type of MRI scanner and enable the selected exposure operating mode corresponding to the type of MRI scanner upon determining the type of MRI scanner. For example, processor 60 may select operating parameters of a first exposure operating mode when the type of MRI scanner is a 1.5 T MRI scanner and select operating parameters of a second exposure operating mode when the type of MRI scanner is a 3.0 T MRI scanner. The selected exposure operating mode may include at least one operating parameter that is specifically tailored for exposure to a particular type of MRI scanner. For example, processor 60 may implement a filter to attenuate signals at a first frequency (e.g., 64 MHz) when operating in the exposure operating mode corresponding to a 1.5 T MRI scanner and implement a filter to attenuate signals at a second frequency (e.g., 128 MHz) when operating in the exposure operating mode corresponding to a 3.0 T MRI scanner.

Additionally or alternatively, processor 60 may control stimulation module 66 to deliver therapy having a different pacing amplitude and/or pulse width based on the type of MRI scanner. Thus, the pacing amplitude and/or pulse width may be tailored for exposure to a specific type of MRI scanner. For example, processor 60 may control stimulation module 66 to adjust the pacing amplitude and/or pulse width by a first amount when IMD 32 is exposed to a 1.5 T MRI scanner and adjust the pacing amplitude and/or pulse width by a second amount when IMD 32 is exposed to a 3.0 T MRI scanner. The first amount may be larger than the second amount or smaller than the second amount. In another aspect, the first amount or second amount may be equal to zero such that the pacing amplitude and/or pulse width are not adjusted for one type of MRI scanner, but adjusted for another type of MRI scanner. In one instance, the adjustment may be an increase in pacing amplitude and/or pulse width.

In some instances, a number of the operating parameters of the exposure operating modes corresponding to the different types of MRI scanners may be the same. Continuing with the example above, the exposure operating modes of the 1.5 T and 3.0 T MRI scanners may have the same pacing mode, pacing amplitude, pacing pulse width, pacing rate, or other operating parameter. As such, although each of the exposure operating modes may include operating parameters specifically tailored for operation in a particular MRI environment, e.g., specific filtering parameters, at least some of the operating parameters of the exposure operating modes may overlap.

As such, processor 60 may begin to operate in accordance with the common exposure mode operating parameters prior to determining the type of MRI scanner and then enable the remaining operating parameters upon determining the specific type of MRI scanner. For example, processor 60 may operate in accordance with the common operating parameters (e.g., pacing mode, pacing pulse amplitude, pacing pulse width, pacing rate, or the like) upon detecting the presence of an MRI scanner and then enable the operating parameters designed for a specific type of MRI scanner (e.g., implement a filter to attenuate RF signals of a particular frequency) upon detecting the type of MRI scanner. In this manner, IMD 32 may reduce the effect of any MRI scanner immediately upon exposure to the MRI scanner and further reduce the effect of a particular type of MRI scanner upon determining the type of MRI scanner.

In another example, processor 60 may operate in accordance with a default exposure operating mode upon detecting the presence of an MRI scanner and then switch to the exposure operating mode corresponding to the specific type of MRI scanner upon detecting the type of MRI scanner. The default exposure operating mode may correspond with an exposure operating mode corresponding to the type of MRI scanner most frequently used, e.g., a 1.5 T MRI scanner. Alternatively, the default exposure operating mode may be an exposure operating mode that includes the common parameters of the two or more exposure operating modes.

Processor 60 may automatically disable the exposure operating mode, e.g., in response to disruptive field detector 68 no longer detecting disruptive energy field 11 of MRI scanner 16, after a predetermined period of time (e.g., one hour), or other condition, or a combination of two or more conditions. In other words, processor 60 may automatically configure IMD 32 from the exposure operating mode back to the normal operating mode based on the one or more conditions. In other instances, a user may manually disable the exposure operating mode of IMD 32, e.g., via interaction with programming device 18. In other words, IMD 32 is manually configured from the exposure operating mode to the normal operating mode upon no longer being exposed to MRI scanner 16.

IMD 32 may use the determination of the type of MRI scanner to adjust one or more parameters that will be used when IMD 32 returns to the normal operating mode upon no longer being exposed to MRI scanner 16. In other words, IMD 32 may adjust one or more parameters of the normal operating mode based on the type of MRI scanner. The adjustment of the one or more parameters of the normal operating mode for use after exposure to MRI scanner 16 may be in addition to or instead of selecting different MRI operating modes. For example, IMD 32 may select one of a plurality of exposure operating modes based on the type of MRI scanner and adjust one or more settings for use in the normal operating mode after exposure to MRI scanner 16 based on the type of MRI scanner. In another example, IMD 32 may select the same exposure operating mode for any type of MRI scanner (e.g., without regard to the type of MRI scanner 16), but adjust one or more settings for use in the normal operating mode after exposure to MRI scanner 16 based on the type of MRI scanner.

IMD 32 may adjust the pacing amplitude and/or pacing pulse width for use when IMD 32 returns to the normal operating mode after exposure to MRI scanner 16, and the amount of adjustment may be determined based on the type of MRI scanner. For example, IMD 32 may adjust the pacing amplitude and/or pulse width by a first amount when exposed to a 1.5 T MRI scanner and adjust the pacing amplitude and/or pulse width by a second amount when exposed to a 3.0 T MRI scanner. The first amount may be larger than the second amount or smaller than the second amount. In another aspect, the first or second amount may be equal to zero. In this manner, the pacing amplitude and/or pulse width may be unchanged when exposed to one type of MRI scanner and adjusted when exposed to another type of MRI scanner. In one instance, the adjustment may be an increase in pacing amplitude and/or pulse width. Such an adjustment may account for changes in pacing thresholds caused by exposure to MRI scanner 16, thereby increasing the efficacy of the therapy.

Other settings used during the normal operating mode may be adjusted based on the type of MRI scanner 16 in addition to or instead of the pacing amplitude or pulse widths. IMD 32 may adjust sensitivity of a sense amplifier of IMD 32 after exposure to MRI scanner 16 and the amount of adjustment may be dependent on the type of MRI scanner in a similar manner as described above with respect to pacing amplitude and/or pulse width. For example, IMD 32 may increase the sensitivity of the sense amplifier by a first amount when exposed to a 1.5 T MRI scanner and increase the sensitivity of the sense amplifier by a second amount when exposed to a 3.0 T MRI scanner. As another example, IMD 32 may decrease the sensitivity of the sense amplifier by a first amount when exposed to a 1.5 T MRI scanner and decrease the sensitivity of the sense amplifier by a second amount when exposed to a 3.0 T MRI scanner. The first amount may be larger than the second amount or smaller than the second amount. In another aspect, the first amount or second amount may be equal to zero. In a further example, IMD 32 may decrease the sensitivity of the sense amplifier when exposed to a first type of MRI scanner and increase the sensitivity of the sense amplifier by a second amount when exposed to a second type of MRI scanner. Such adjustments may account for changes in sensing thresholds caused by exposure to MRI scanner 16.

Prior to enabling the exposure operating mode, processor 60 operates IMD 32 in accordance with settings programmed by a physician, electrophysiologist, clinician or other user, referred to herein as the normal operating mode. The normal operating mode may correspond with the operating mode that a physician or other user feels provides a most efficacious therapy for patient 12. The normal operating mode may vary from patient to patient depending on the condition of patient 12 for which IMD 32 is providing therapy. In some instances, the normal operating mode may be adaptive in that the normal operating mode actually includes switching between more than one pacing mode based on the condition of the patient, such as described in U.S. Pat. No. 7,130,683 to Casavant et al., entitled, "PREFERRED ADI/R: A PERMANENT PACING MODE TO ELIMINATE VENTRICULAR PACING WHILE MAINTAINING BACKUP SUPPORT," which issued on Oct. 31, 2006 and which is incorporated herein by reference in its entirety.

The normal operating mode of IMD 32 may be one or more of any of a number of pacing modes, including DDD, VVI, DVI, VDD, AAI, DDI, DDDR, VVIR, DVIR, VDDR, AAIR, DDIR, VOO, AOO, DOO, ODO and other modes of single and dual-chamber pacing or sensing. For example, the normal operating mode may be an atrial based pacing mode, such as AAI or ADI pacing mode, if IMD 32 is providing therapy to a patient experiencing bradycardia. As another example, the normal operating mode may be a dual-chamber pacing mode, such as a DDD pacing mode, if IMD 32 is providing therapy to a patient with unreliable A-V conduction.

In the aforementioned operating modes, the abbreviations of which conform to the NBG Pacemaker Code, the first letter in the pacing mode indicates the chamber or chambers paced and may take on the letter "D" indicating dual-chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual-chamber (i.e., atrial and ventricle both paced), "V" indicating a ventricle is paced, "A" indicating an atrium is paced, or "O" indicating no chamber is paced. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

When IMD 32 is configured to generate and deliver therapy to heart 38, control processor 60 controls stimulation module 66 to deliver electrical stimulation therapy to heart 38 via one or more of electrodes 44, 46, 50, 52 and/or the housing electrode. Stimulation module 66 is electrically coupled to electrodes 44, 46, 50 and 52, e.g., via conductors of the respective lead 34 and 36, or, in the case of the housing electrode, via an electrical conductor disposed within the housing of IMD 32. Control processor 60 controls stimulation module 66 to generate and deliver electrical pacing pulses with the amplitudes, pulse widths, rates, electrode combinations or electrode polarities specified by a selected therapy program. For example, electrical stimulation module 66 may deliver bipolar pacing pulses via ring electrodes 46 and 52 and respective corresponding helical tip electrodes 44 and 50 of leads 34 and 36, respectively. Stimulation module 66 may deliver one or more of these types of stimulation in the form of other signals besides pulses or shocks, such as sine waves, square waves, or other substantially continuous signals. In addition to pacing pulses, stimulation module 66 may, in some instances, deliver other types of electrical therapy, such as defibrillation, cardioversion and/or cardiac resynchronization therapy.

Processor 60 may include a pacer timing and control module (not shown), which may be embodied as hardware, firmware, software, or any combination thereof. The pacer timing and control module may comprise a dedicated hardware circuit, such as an ASIC, separate from other components of control processor 60, or comprise a software module executed by a component of control processor 60, which may be a microprocessor or ASIC. In other instances, the pacer timing and control module may be part of stimulation module 66.

The pacer timing and control module may include programmable counters which control the basic time intervals associated with various single and dual-chamber pacing modes. Intervals defined by the pacer timing and control module within control processor 60 may include, for example, atrial and ventricular pacing escape intervals and refractory periods during which sensed atrial and ventricular events are ineffective to restart timing of the escape intervals. As another example, the pace timing and control module may define a blanking period, and provide signals to sensing module 62 to blank one or more channels, e.g., amplifiers, for a period during and after delivery of electrical stimulation to heart 38. The durations of these intervals may be determined by control processor 60 in response to parameters of the operating mode, which are stored in memory 72. The pacer timing and control module of control processor 60 may also determine the amplitude and pulse width of the cardiac pacing pulses.

During pacing, escape interval counters within the pacer timing and control module of control processor 60 may be reset upon sensing of R-waves and P-waves with detection channels of sensing module 62. Additionally, the value of the count present in the escape interval counters when reset by sensed R-waves and P-waves may be used by control processor 60 to measure the durations of R-R intervals, P-P intervals, P-R intervals and R-P intervals, which are measurements that may be stored in memory 72. Control processor 60 may analyze these various intervals to determine conditions of heart 38, such as to detect a tachyarrhythmia event. When IMD 32 is capable of providing defibrillation therapy, the R-R intervals may be used to increment a VF counter to control delivery of cardioversion or defibrillation shocks. For example, the VF counter may be incremented in response to detection of short R-R intervals, and possibly in response to other events such as R-R interval variance. The VF counter triggers delivery of a defibrillation shock when the counter reaches a number of intervals for detection (NID) threshold. Additionally, control processor 60 may begin an anti-tachyarrhythmia pacing regimen prior to delivery of the defibrillation shock.

Sensing module 62 is configured to receive signals from one or more sensors. In one example, sensing module 62 is configured to receive signals sensed by one or more of electrodes 44, 46, 50, 52 and the housing electrode. In this manner, electrodes 44, 46, 50, 52, and the housing electrode may operate as sense electrodes in addition to or instead of being used for delivering electrical stimulation therapy. In other instances, leads 34 and 36 may include one or more electrodes dedicated for sensing. In further examples, sensing module 62 is coupled to one or more sensors that are not included on leads 34 and 36, e.g., via a wired or wireless coupling. Such sensors may include, but are not limited to, pressure sensors, accelerometers, flow sensors, blood chemistry sensors, activity sensors or other type of physiological sensor. Signals monitored by sensing module 62 may be stored in memory 72.

Sensing module 62 may include one or more detection channels, each of which may comprise a sense amplifier. The detection channels may be used to sense cardiac signals. Some detection channels may detect events, such as R- or P-waves, and provide indications of the occurrences of such events to processor 60. One or more other detection channels may provide the signals to an analog-to-digital converter, for processing or analysis by processor 60. In response to the signals from processor 60, a switch module (not shown) within sensing module 62 may couple selected electrodes to selected detection channels.

For example, sensing module 62 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 60 then uses that detection in measuring frequencies of the sensed events. Different narrow band channels of sensing module 62 may have distinct functions. For example, some various narrow band channels may be used to sense either atrial or ventricular events.

In one example, at least one narrow band channel may include an R-wave amplifier that receives signals from the sensing configuration of electrodes 44 and 46, which are used for sensing and/or pacing in right ventricle 42 of heart 38. In addition, in some examples, a narrow band channel may include a P-wave amplifier that receives signals from electrodes 50 and 52, which are used for pacing and sensing in right atrium 40 of heart 38. The R-wave and P-wave amplifier may take the form of an automatic gain controlled amplifier that provides an adjustable sensing threshold. Other amplifiers may also be used. Furthermore, in some examples, one or more of the sensing channels of sensing module 62 may be selectively coupled to the housing electrode, with or instead of one or more of electrodes 44, 46, 50 or 52, e.g., for unipolar sensing of R-waves or P-waves.

In some examples, sensing module 62 includes a wide band channel which may comprise an amplifier with a relatively wider pass band than the R-wave or P-wave amplifiers. Signals from the sensing electrodes that are selected for coupling to this wide-band amplifier may be converted to multi-bit digital signals by an analog-to-digital converter provided by, for example, sensing module 62 or processor 60. In some examples, processor 60 may store the digitized versions of signals from the wide band channel as electrograms (EGMs) in memory 72. Processor 60 may employ digital signal analysis techniques to characterize the digitized signals from the wide band channel to, for example detect and classify the patient's heart rhythm. Processor 60 may detect and classify the patient's heart rhythm by employing any signal processing methodologies appropriate for the intended application or applications of IMD 32. Processor 60 may then control stimulation module 66 based on the signals sensed by sensing module 62.

As described above, the normal operating mode of IMD 32 may be susceptible to undesirable operation when IMD 32 is placed within environment 10 with disruptive energy field 11. In some instances, sensing module 62 inappropriately detects the induced energy on the leads as physiological signals (e.g., intrinsic cardiac events). In other words, IMD 32 senses a physiological signal when one is not actually present. At the very least, the detection of the induced energy caused by disruptive energy field 11 results in the stored data not accurately representing the actual function and condition of heart 38. Moreover, the detection of the induced energy caused by disruptive energy field 11 may in turn cause undesirable operation of IMD 32.

For example, when the current or normal operating mode is a pacing mode with inhibit response to sensing, processor 60 may not deliver (i.e., withhold) a desired pacing pulse in response to sensing the induced energy from disruptive energy field 11 as a physiological signal. For example, processor 60 may identify the induced energy as a ventricular event. This may result in control processor 60 resetting the ventricular escape interval counter, thereby inhibiting delivery of a desired pacing pulse. In other instances when the normal operating mode is a dual chamber pacing mode with inhibit and trigger response to sensing, processor 60 may also deliver an undesirable pacing pulse in addition to withholding a desired pacing pulse in response to sensing the induced energy from disruptive energy field 11 as a physiological signal. In particular, sensing the induced energy from the disruptive energy field as a physiological signal may inappropriately start an escape interval after which an undesired pacing pulse is delivered. This may result in dangerously fast heart rhythms and may lead to tachyarrhythmia or fibrillation.

In other instances, the induced energy on the leads may result in IMD 32 not sensing actual physiological signals that are present. Processor 60 may, for example, initiate a blanking period in response to the induced energy on the leads. During the blanking period, sensing module 62 may power down one or more sense amplifiers. As such, sensing module 62 will fail to detect any intrinsic physiological event that occurs during the blanking period. Failure to detect this actual physiological event may again result in IMD 32 delivering undesired therapy or withholding desired therapy.

In further instances, the induced energy on one or more of leads 34 and 36 or on one or more components of IMD 32 may result in inadvertent stimulation or heating of the tissue and/or nerve site adjacent to any of electrodes 44, 46, 50 and 52 of respective leads 34 and 36 or the housing of IMD 32. Such heating may compromise pacing and sensing thresholds at the tissue site, which could result in reduced therapy efficacy.

To reduce the adverse effects of disruptive energy field 11, control processor 60 may be configured to operate IMD 32 in the exposure operating mode as described in detail above. The exposure operating mode is typically less susceptible to undesirable operation in disruptive energy field 11 than the normal operating mode. In other words, operating IMD 32 in the exposure mode may reduce, if not eliminate, some or all of the adverse effects that disruptive energy field 11 have on therapy delivery to patient 12. When operating in the exposure operating mode, control processor 60 is configured to operate with different functionality compared to the normal operating mode. Processor 60 may, in some instances, be configured to operate with reduced functionality. For example, processor 60 may not provide sensing, not deliver therapy, delivery only a subset of possible therapies, not log collected data or the like. In other instances, processor 60 may be operating with approximately the same functionality or even increased functionality in the exposure mode. For example, processor 60 may use a different sensor or algorithm to detect cardiac activity of the heart of patient 12, such as pressure sensor measurements rather than electrical activity of the heart.

Processor 60 may receive the parameters of the exposure operating mode from a user via programming device 18. In other words, the exposure operating mode parameters may be manually configured by the user. In another example, at least a portion, and in some cases all, of the parameters of the exposure operating mode may be automatically determined One example technique for automatically determining one or more parameters of the exposure operating mode is described in co-pending patent application Ser. No. 12/569,101 to Ellingson et al., entitled, "AUTOMATIC SELECTION OF PARAMETERS OF AN EXPOSURE MODE OF AN IMPLANTABLE MEDICAL DEVICE," which was filed on Sept. 29, 2009 and which is incorporated herein by reference in its entirety. Whether the parameters were manually entered or automatically determined or both, processor 60 may store the parameters of the exposure operating mode in memory 72.

Control processor 60 may include any one or more of a microprocessor, a controller, a DSP, ASIC, FPGA, or equivalent discrete or integrated circuitry, including analog circuitry, digital circuitry, or logic circuitry. The functions attributed to control processor 60 herein may be embodied as software, firmware, hardware or any combination thereof.

Memory 72 may include computer-readable instructions that, when executed by control processor 60 or other component of IMD 32, cause one or more components of IMD 32 to perform various functions attributed to those components in this disclosure. Memory 72 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

The various components of IMD 32 are coupled to power source 74, which may include a rechargeable or non-rechargeable battery. A non-rechargeable battery may be capable of holding a charge for several years, while a rechargeable battery may be inductively charged from an external device, e.g., on a daily or weekly basis. Power source 74 also may include power supply circuitry for providing regulated voltages and/or current levels to power the various components of IMD 32.

Under the control of processor 60, telemetry module 70 may receive downlink telemetry from and send uplink telemetry to programming device 18 with the aid of an antenna 78, which may be internal and/or external to IMD 32. Telemetry module 70 includes any suitable hardware, firmware, software or any combination thereof for communicating with another device, such as programming device 18. For example, telemetry module 70 may include appropriate modulation, demodulation, encoding, decoding, frequency conversion, filtering, and amplifier components for transmission and reception of data.

The various modules of IMD 32 may include one or more processors, such as one or more microprocessors, DSPs, ASICs, FPGAs, programmable logic circuitry, or the like, that may perform various functions and operations, such as those described herein.

Figure 4:
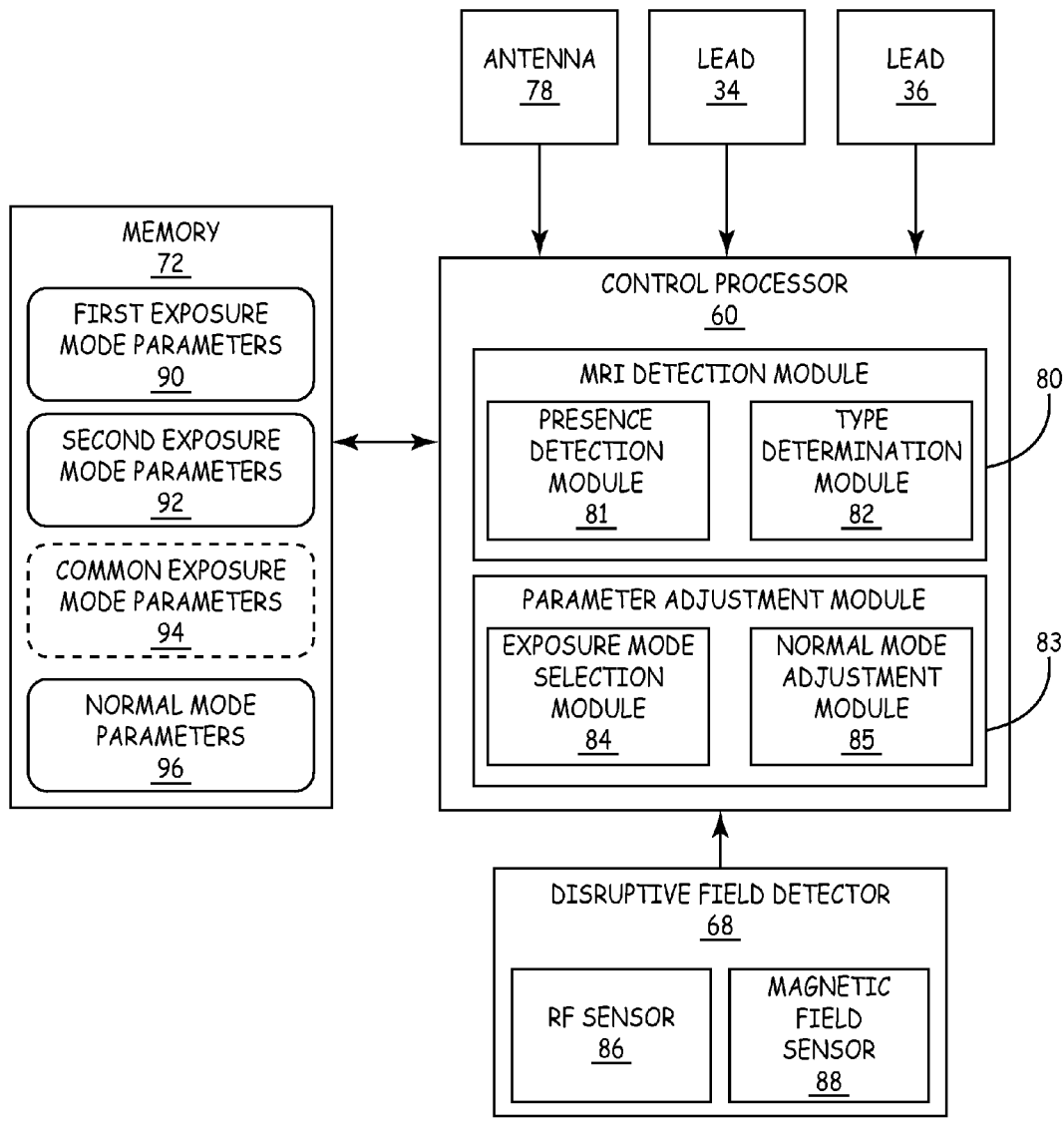
FIG. 4 is a functional block diagram illustrating some of the components of the IMD of FIG. 3 in further detail.

FIG. 4 is a functional block diagram illustrating control processor 60, disruptive field detector 68 and memory 72 in further detail. Processor 60 of FIG. 4 includes an MRI detection module 80 having a presence detection module 81 and a type determination module 82 and a parameter adjustment module 83 having an exposure mode selection module 84 and a normal mode adjustment module 85. Disruptive field detector 68 of FIG. 4 includes an RF sensor 86 and a magnetic field sensor 88. Control processor 60, memory 72 and/or disruptive field detector 68 may include more or fewer components based on particular implementation of the techniques of this disclosure.

MRI presence detection module 81 of processor 60 detects a condition indicative of the presence of MRI scanner 16. MRI presence detection module 81 inputs signals from one or more of disruptive field detector 68, antenna 78, lead 34 or lead 36. MRI presence detection module 81 detects a condition indicative of the presence of MRI scanner 16 based on the signals. In one example, MRI presence detection module 81 may detect the condition indicative of the presence of MRI scanner 16 based on input from magnetic field sensor 88, which may vary as a function of the magnitude of the magnetic field. MRI presence detection module 81 may detect the condition indicative of the presence of MRI scanner 16 when the signal from magnetic field sensor 88 exceeds a threshold. Magnetic field sensor 88 may, for example, comprise a Hall effect sensor, magnetoresistive sensor or other magnetic field sensor. MRI presence detection module 81 may, however, detect the presence of MRI scanner 16 using other signals detected by any one of or a combination of disruptive field detector 68, antenna 78, lead 34 or lead 36.

MRI type determination module 82 determines a type of MRI scanner in response to detecting the presence of MRI scanner 16. MRI type determination module 82 inputs signals from one or more of disruptive field detector 68, antenna 78, lead 34 or lead 36 and analyzes the signals to determine the type of MRI scanner. In one example, MRI type determination module 82 may determine the type of MRI scanner based on the same signals used by MRI presence detection module 81 for detecting the presence of MRI scanner 16. MRI type determination module 82 may determine that MRI scanner 16 is a 1.5 T MRI scanner if the output of magnetic field sensor 88 is in a first range and determine MRI scanner 16 is a 3.0 T MRI scanner when the output of magnetic field sensor 88 is in a second range. As such, MRI type determination module 82 may determine the type of MRI scanner based on the same signals used to detect the condition indicative of the presence of MRI scanner 16. In some instances, MRI presence detection module 81 and MRI type determination module 82 may be viewed as concurrently detecting the presence and type of MRI scanner 16, respectively. In such a case, MRI presence detection module 81 and MRI type determination module 82 may be a single module.

In another example, MRI type determination module 82 determines the type of MRI scanner based on signals from one or more other sources in addition to or instead of the signals received from magnetic field sensor 88. For instance, upon detecting the condition indicative of the presence of MRI scanner 16 (e.g., magnitude of magnetic field exceeds a threshold), MRI type determination module 82 may determine a frequency of RF energy emitted subsequent to detecting the presence of MRI scanner 16 to determine the type of scanner. MRI type determination module 82 may determine that the MRI scanner is a 1.5 T scanner when the frequency of RF energy is approximately 64 MHz and determine that the MRI scanner is a 3.0 T MRI scanner when the frequency of the RF energy is approximately 128 MHz.

To this end, MRI type determination module 82 receives input from one or more components that receive the RF energy emitted by MRI scanner 16. For example, MRI type determination module 82 may receive input from RF sensor 86 of disruptive field detector 68. RF sensor 86 may include one or more coils, stubs, or other structure that operates as an antenna to receive RF energy. The structures or "antennas" of RF sensor 86 may be tuned to a frequency that is approximately equal to the frequency of the RF energy of the MRI scanner (e.g., 64 or 128 MHz in the case of a 1.5 T or 3.0 T MRI scanner). RF sensor 86 may also include a frequency detector that may, for example, determine when the energy induced on the antennas of RF sensor 86 exceeds a threshold. RF sensor 86 may send a signal to processor 86 indicating that RF energy of a particular frequency has been detected. Alternatively, the frequency detection circuitry may be implemented within MRI type determination module 82 and RF sensor 86 simply passes the induced energy to MRI type determination module 82 for determination as to whether RF energy of a particular frequency is detected.

As another example, MRI type determination module 82 may receive a signal from antenna 78 and use that signal to determine whether RF energy of a particular frequency (e.g., RF energy of a frequency corresponding to a particular type of MRI scanner) is received. Although antenna 78 may not be tuned to the frequency utilized by MRI scanner 16, the pulsed RF signals of MRI scanner 16 may induce a signal on antenna 78. MRI type determination module 82 may determine the frequency of the RF energy using the signal induce on antenna 78 to identify the type of MRI scanner.

In another example, MRI type determination module 82 may receive a signal from one of leads 34 or 36 and use that signal to determine whether RF energy of a particular frequency (e.g., RF energy of a frequency corresponding to a particular type of MRI scanner) is received. Conductors within leads 34 and 36 may act as an antenna when placed in environment 10. In other words, the pulsed RF signals of MRI scanner 16 may induce a signal on one of more of the conductors within leads 34 or 36. MRI type determination module 82 may analyze the induced signals on conductors of leads 34 or 36 to determine the frequency of the RF energy and identify the type of MRI scanner. MRI type determination module 82 may, in some instances, determine the frequency of the RF energy using multiple sources, i.e., a combination of RF sensor 86, antenna 78, lead 34 or lead 36, or other mechanism for determining the frequency of RF energy. MRI type determination module 82 may also use the various sources as an antenna diversity scheme for use in detecting the type of MRI device.

In the examples described above, MRI presence detection module 81 may detect the presence of MRI scanner 16 based on the existence of a strong magnetic field and MRI type determination module 82 may determine the type of MRI scanner based on the frequency of RF energy. MRI presence detection module 81 may, however, detect the presence of MRI scanner 16 using other signals detected by any one or a combination of disruptive field detector 68, antenna 78, lead 34 or lead 36. Likewise, MRI type determination module 82 may determine the type of MRI scanner using other signals detected by any one of or a combination of disruptive field detector 68, antenna 78, lead 34 or lead 36.

Based on the determination of the type of MRI scanner, exposure mode selection module 84 may select an appropriate exposure operating mode, e.g., by retrieving exposure mode operating parameters corresponding to the type of MRI scanner, and configure IMD 32 to operate in accordance with the retrieved operating parameters. For example, exposure mode selection module 84 may retrieve first exposure mode operating parameters 90 from memory 72 in response to determining that the MRI scanner is a 1.5 T MRI scanner and select second exposure mode operating parameters 92 from memory 72 in response to determining that the MRI scanner is a 3.0 T MRI scanner.

As described above, first exposure mode operating parameters 90 and second exposure mode operating parameters 92 include at least one operating parameter that is specifically tailored for exposure to a particular type of MRI scanner. For example, processor 60 may implement a filter to attenuate signals at a first frequency (e.g., 64 MHz) when operating in the exposure operating mode corresponding to a 1.5 T MRI scanner and implement a filter to attenuate signals at a second frequency (e.g., 128 MHz) when operating in the exposure operating mode corresponding to a 3.0 T MRI scanner. Additionally or alternatively, processor 60 may control stimulation module 66 to deliver therapy having a different pacing amplitude and/or pulse width based on the type of MRI scanner as described in detail above.

However, exposure mode operating parameters 90 and 92 may include some common operating parameters. In other words, some parameters of operating parameters 90 and 92 may be the same regardless of the type of MRI scanner. For example, exposure mode operating parameters 90 and 92 may include the same pacing mode, pacing amplitude, pacing pulse width, pacing rate, or other operating parameter. As such, although each of the exposure operating modes may include operating parameters specifically tailored for operation in a particular MRI environment, exposure mode operating parameters 90 and 92 may include at least some operating parameters in common.

Because of the commonality in some (or many) of the operating parameters of the different exposure operating modes, processor 60 may configure IMD 32 to operate in accordance with the common operating parameters prior to determining the type of MRI scanner. For example, processor 60 may retrieve common exposure mode operating parameters 94 from memory 72 upon detecting the presence of an MRI scanner (e.g., upon detecting a large static magnetic field) and then retrieve the operating parameters 90 or 92 that are specific to the type of MRI scanner upon detecting the type of MRI scanner (e.g., based on the frequency of the RF energy). In this manner, processor 60 may reduce the effect of any MRI scanner immediately upon exposure to the MRI scanner and further reduce the effect of the particular type of MRI scanner upon determining the type of MRI scanner.

In other aspects, normal mode adjustment module 85 may adjust one or more parameters to use when IMD 32 returns to the normal operating mode after exposure to MRI scanner 16. Normal mode adjustment module 85 may, for example, determine the parameter or parameter(s) to adjust and the amount of adjustment necessary based on the type of MRI scanner. The normal operating mode parameters 96 may be stored in memory 72 and normal mode adjustment module 85 may read and write new values to normal operation mode parameters 96 of memory 72 based on the type of MRI scanner. Normal mode adjustment module 85 may, for example, adjust one or more of a pacing amplitude, pacing pulse width, a sensitivity of a sense amplifier or other parameter that is used during the normal operating mode.

The adjustment of the one or more parameters for use in the normal operating mode after exposure to MRI scanner 16 may be in addition to or instead of selecting different MRI operating modes. For example, IMD 32 may select one of a plurality of exposure operating modes based on the type of MRI scanner and adjust one or more settings for use in the normal operating mode after exposure to MRI scanner 16 based on the type of MRI scanner. In another example, IMD 32 may select the same exposure operating mode for any type of MRI scanner (e.g., without regard to the type of MRI scanner 16), but adjust one or more settings for use in the normal operating mode after exposure to MRI scanner 16 based on the type of MRI scanner.

Figure 5:
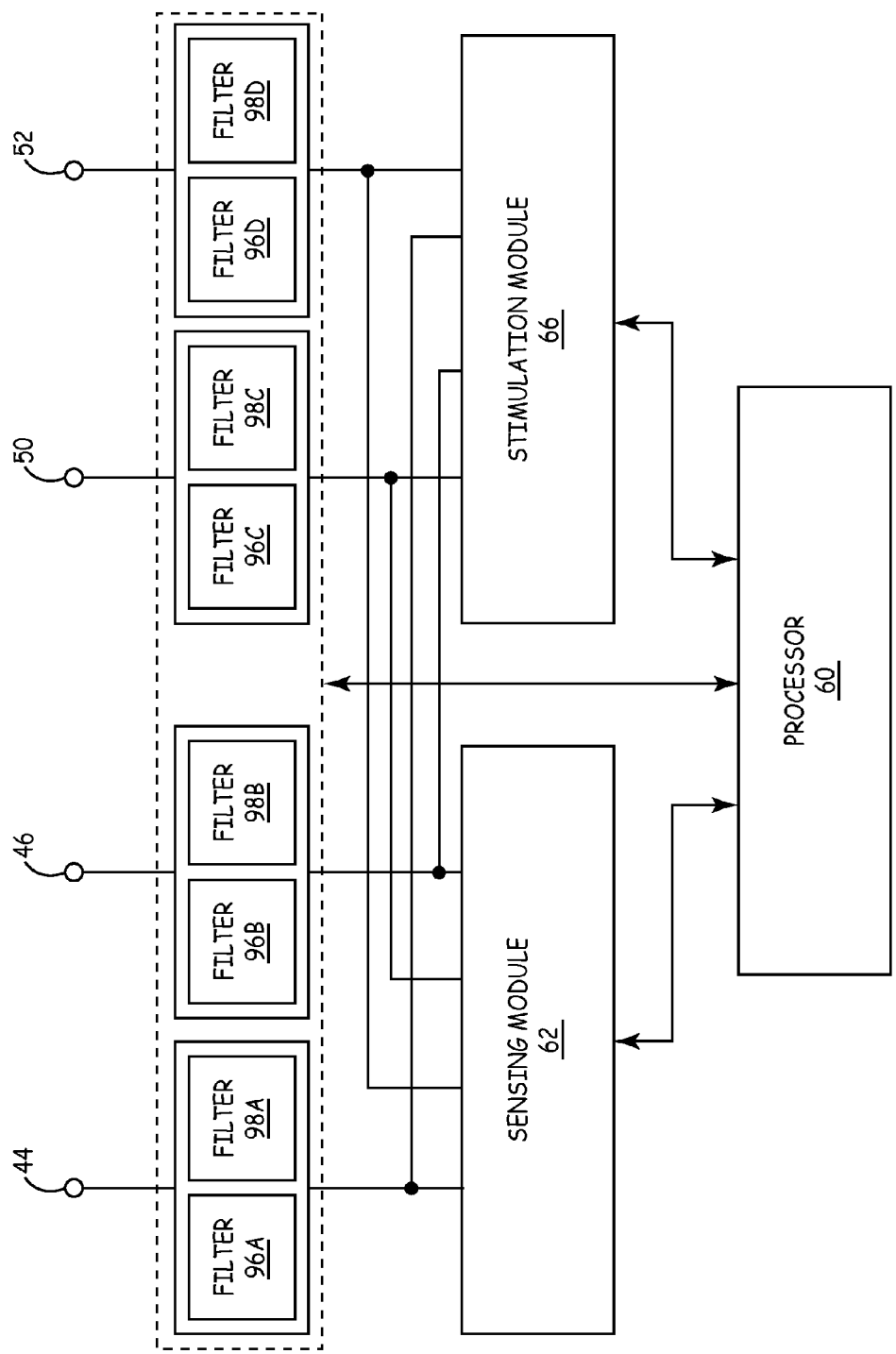
FIG. 5 is a functional block diagram illustrating example components for implementing exposure operating modes tailored for specific types of MRI scanners.

FIG. 5 is a functional block diagram illustrating example components of IMD 32 for implementing exposure operating modes tailored for specific types of MRI scanners. As described in detail above, processor 60 determines the type of MRI scanner based on one or more detected conditions. In response to determining the type of MRI scanner, processor 60 may retrieve operating mode parameters corresponding to the type of MRI scanner and configure IMD 32 to operate in accordance with the retrieved operating parameters.

IMD 32 may, in one example, include filters 96A-96D and filters 98A-98D (collectively "filters 96" and "filters 98," respectively). In the example illustrated in FIG. 5, filters 96 and 98 are coupled between respective electrodes of leads 34 and 36 and sensing module 62 and stimulation module 66. For example, filter 96A and 98A are connected between electrode 44 of lead 34 and modules 62 and 66. Likewise, filters 96B and 98B are connected between electrode 46 of lead 34 and modules 62 and 66, filters 96C and 98C are connected between electrode 50 of lead 36 and modules 62 and 66, and filter 96D and 98D are connected between electrode 52 of lead 36 and modules 62 and 66. Each of filters 96 is configured to suppress signals with frequencies approximately equal to 64 MHz and each of filters 98 is configured to suppress signals with frequencies approximately equal to 128 MHz. In one example, filters 96 and 98 may be band-stop filters, such as notch filters, designed to suppress signals around the desired frequencies, e.g., 64 MHz and 128 MHz, respectively.

Upon determining the type of MRI scanner, processor 60 selects the appropriate ones of filters 96 and 98 based on the type of MRI scanner and applies the selected filter to signals on conductors of leads 34 and 36. For a 1.5 T scanner, which generates pulsed RF energy at 64 MHz, processor 60 may apply filters 96A-96D to the signals on the respective conductors to which filters 96 are connected. For a 3.0 T scanner, which generates pulsed RF energy at 128 MHz, processor 60 may apply filters 98A-98D to the signals on the respective conductors to which filters 98 are connected. In this manner, the exposure operating mode is tailored for the type of MRI scanner that is detected.

Filters 96 and 98 may, in one example, be absorptive filters that absorb the unwanted RF energy. In this case, filters 96 and 98 absorb the RF energy into the device instead of reflecting the RF energy back toward the electrodes on leads 34 and 36. Absorbing the RF energy at the device may reduce the amount of heating that occurs adjacent to electrodes 44, 46, 50 and 52 of leads 34 and 36. In another example, filters 96 and 98 may be reflective filters that reflect the unwanted RF energy away from the device. In either case, the RF energy induced on leads 34 and 36 is attenuated, thus increasing the accuracy with which sensing module 62 may sense cardiac signals of heart 38. Prior to operating IMD 32 in one of the exposure operating modes, signals on conductors of leads 34 and 36 may go unfiltered into sensing module 62 or filtered using filter feed through capacitors in the connector block 54.

Filters 96 and 98 may include one or more capacitive elements, inductive elements and resistive elements. In some instances, each of filters 96 and 98 may be separate components, e.g., include separate capacitive, inductive and resistive elements. Processor 60 may switch between the filters based on the type of MRI scanner. In other instances, filters 96 may share one or more capacitive, inductive or resistive elements with corresponding filter 98. For example, filter 96A and 98 may share one or more capacitive, inductive or resistive elements. In this case, processor may switch in one or more additional elements or adjust the shared elements to tune the filters to the appropriate frequency based on the type of MRI. The capacitive, inductive and resistive elements may be discrete components or may be intrinsic characteristics of components that also serve an additional purpose, such as channel capacitors, laser ribbon bonds, feed through capacitors, or some intrinsic property of another component of IMD 32.

Filters 96 and 98 may be located within a housing of IMD 32, within a connector block of IMD 32, or partially located within the housing and the connector block. In other instances, filters 96 and 98 may be located within the body of leads 34 and 36, e.g., at a proximal end near IMD 32 or at a distal end near electrodes of leads 34 and 36.

Figure 6:
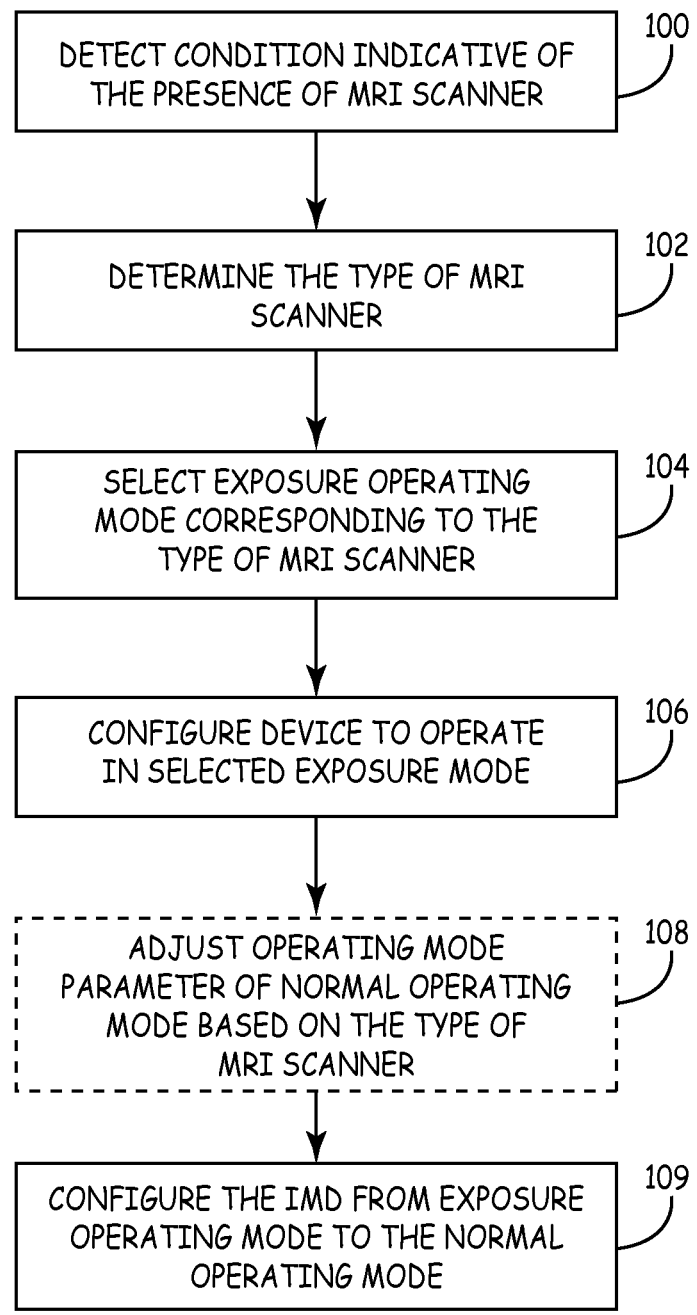
FIG. 6 is a flow diagram illustrating an example operation of an IMD selecting an exposure operating mode based on the type of MRI scanner.

FIG. 6 is a flow diagram illustrating an example operation of an IMD, such as IMD 32 or IMD 14, selecting an exposure operating mode based on the type of MRI scanner. In FIG. 6, processor 60 of IMD 32 detects a condition indicative of a presence of MRI scanner 16 (100). Presence detection module 82 of processor 60 may receive a signal from one or more sources, including disruptive field detector 68, antenna 78, lead 34 or lead 36 and analyze the signal to detect the condition indicative of the presence of MRI scanner 16. In one example, presence detection module 81 may detect the presence of MRI scanner 16 upon detecting a magnetic field having a magnitude that is larger than a threshold.

Processor 60 determines the type of MRI scanner (102). Type determination module 82 of processor 60 may determine the type of MRI scanner based on the signals used to detect the presence of MRI scanner 16, based on one or more other signals or based on the signals used to detect the presence of MRI scanner 16 and one or more other conditions. For example, type determination module 82 may determine that MRI scanner 16 is a 1.5 T MRI scanner when the magnetic field has a magnitude within a first threshold range corresponding to the 1.5 T MRI scanner and determine that MRI scanner 16 is a 3.0 T MRI scanner when the magnetic field has a magnitude within a first threshold range corresponding to the 3.0 T MRI scanner. As another example, type determination module 82 may determine the type of MRI scanner based a frequency of RF energy generated by MRI scanner 16. Type determination module 82 may determine that the MRI scanner is a 1.5 T scanner when the frequency of RF energy is approximately 64 MHz and determine that the MRI scanner is a 3.0 T MRI scanner when the frequency of the RF energy is approximately 128 MHz.

Processor 60 selects an exposure operating mode corresponding to the type of MRI scanner (104). For example, exposure mode selection module 84 of processor 60 may select operating parameters of a first exposure operating mode for a 1.5 T MRI scanner and select operating parameters of a second exposure operating mode for a 3.0 T MRI scanner. The selected exposure operating mode may include at least one operating parameter that is specifically tailored for exposure to a particular type of MRI scanner. For example, processor 60 may implement a filter to attenuate signals at a first frequency (e.g., 64 MHz) when operating in the exposure operating mode corresponding to a 1.5 T MRI scanner and implement a filter to attenuate signals at a second frequency (e.g., 128 MHz) when operating in the exposure operating mode corresponding to a 3.0 T MRI scanner. However, some of the operating parameters may be the same for each of the exposure operating modes, such as the pacing mode, pacing pulse amplitude, pacing pulse width, pacing rate, or the like. Processor 60 configures IMD 32 to operate in the selected exposure operating mode corresponding to the type of MRI scanner (106).

Processor 60 may adjust one or more parameters of the normal operating mode based on the determination of the type of MRI scanner (108). In other words, processor 60 may adjust one or more parameters for use when IMD 32 returns to the normal operating mode after exposure to MRI scanner 16. For example, normal mode adjustment module 85 may adjust the one or more parameter of the normal operating mode by a first amount when exposed to a first type of MRI scanner (e.g., a 1.5 T MRI scanner) and adjust the parameter by a second amount when exposed to a second type of MRI scanner (e.g., a 3.0 T MRI scanner). The first amount may be larger than the second amount or smaller than the second amount. In another aspect, the first or second amount may be equal to zero such that the parameter is unchanged when exposed to one type of MRI scanner and adjusted when exposed to another type of MRI scanner. The one or more parameters of the normal operating mode may include, for example, a pacing amplitude, a pacing pulse width, a sensitivity of a sense amplifier or other parameter that may need to be changed due to the exposure of IMD 32 to MRI scanner 16. Processor 60 may, in some instances, not adjust any parameters of the normal operating mode based on the determination of the type of MRI scanner.

Processor 60 configures IMD 32 from the exposure operating mode to the normal operating mode after completion of the MRI scan (109). In one example, processor 60 may automatically configure IMD 32 from the exposure operating mode to the normal operating mode, e.g., in response to disruptive field detector 68 no longer detecting disruptive energy field 11 of MRI scanner 16, after a predetermined period of time (e.g., one hour), or other condition, or a combination of two or more conditions. In another example, processor 60 may configure IMD 32 from the exposure operating mode to the normal operating mode manually via interaction with programming device 18.

Figure 7:
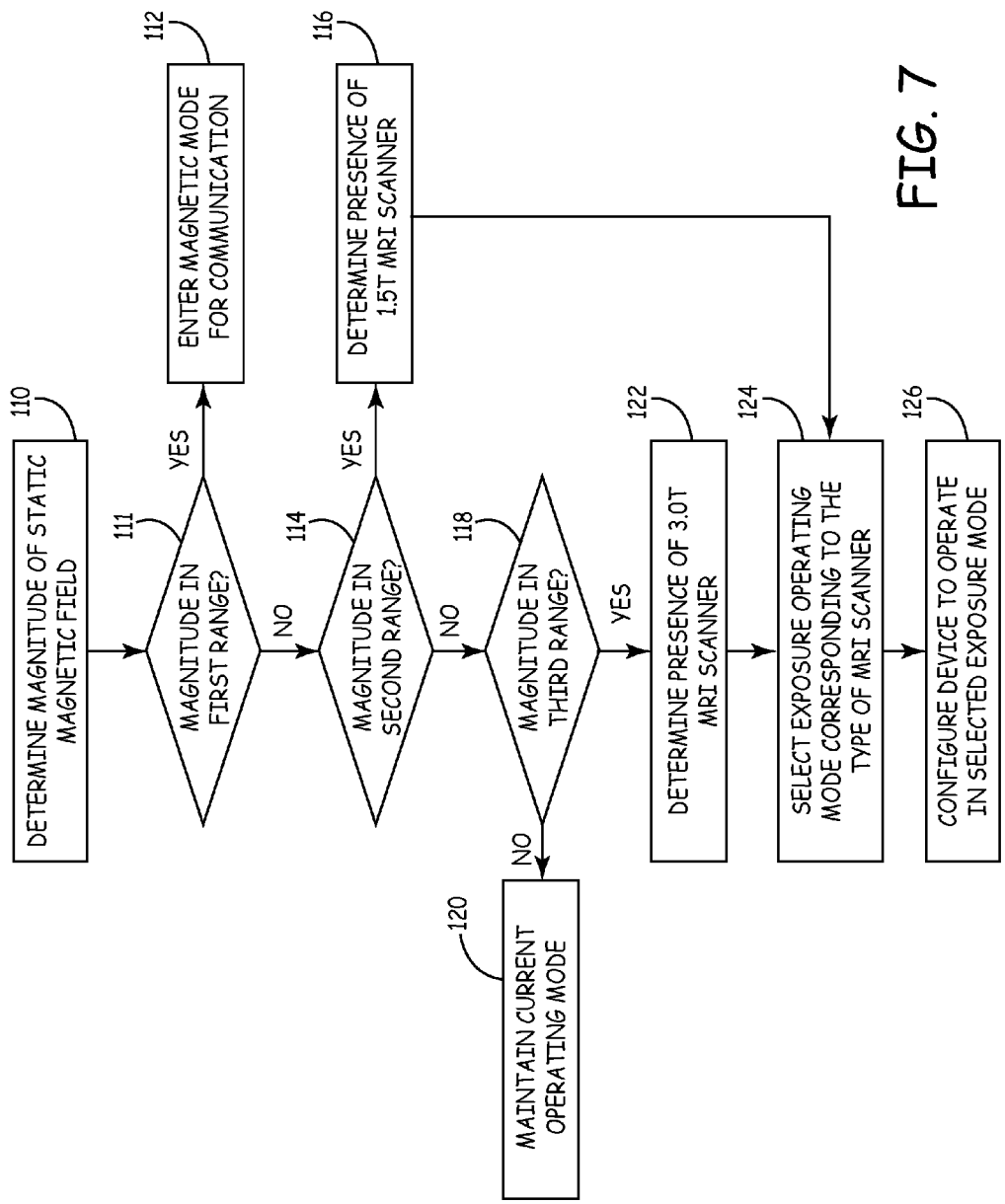
FIG. 7 is a flow diagram illustrating an example operation of an IMD detecting the presence of an MRI scanner and determining the type of MRI scanner.

FIG. 7 is a flow diagram illustrating an example operation of an IMD, such as IMD 32 or IMD 14, detecting the presence of an MRI scanner and determining the type of MRI scanner. Processor 60 of IMD 32 determines a magnitude of a static magnetic field to which IMD 32 is exposed (110). Processor 60 may, for example, obtain a signal from magnetic field sensor 88, which may vary as a function of the magnitude of the magnetic field, and analyze the signal to determine the magnitude of the magnetic field.

Processor 60 determines whether the magnitude of the static magnetic field is within a first range (111). The first range may correspond with a magnitude range of a magnet mode of operation. When processor 60 determines that the magnitude of the static magnetic field is within the first range, processor 60 configures IMD 32 to operate in accordance with the magnet mode (112). The magnetic mode of operation may correspond with an asynchronous pacing mode (e.g., DOO or VOO) and may be used when a user wishes to establish communication with IMD 32, such as during a follow-up visit.

When processor 60 determines that the magnitude of the static magnetic field is not within the first range, processor 60 determines whether the magnitude of the static magnetic field is within a second range (114). The second range may correspond with a magnitude range of a first type of MRI scanner, e.g., a 1.5 T MRI scanner. When processor 60 determines that the magnitude of the static magnetic field is within the second range, MRI presence detection module 81 determines the presence of a 1.5 T MRI scanner (116).

When processor 60 determines that the magnitude of the static magnetic field is not within the second range, processor 60 determines whether the magnitude of the static magnetic field is within a third range (118). The third range may correspond with a magnitude range of a second type of MRI scanner, e.g., a 3.0 T MRI scanner. When processor 60 determines that the magnitude of the static magnetic field is within the third range, MRI presence detection module 81 determines the presence of a 3.0 T MRI scanner (122). In this manner, processor 60 may be viewed as concurrently detecting the presence and type of MRI scanner based on the magnitude of the magnetic field. If the magnitude of the magnetic field does not fall within any of the three ranges, processor 60 determines that no MRI scanner is present and maintains operating in accordance with the current (or normal) operating mode (120).

In response to detecting the presence and type of MRI scanner, processor 60 selects an exposure operating mode corresponding to the type of MRI scanner (124). For example, processor 60 may select operating parameters of a first exposure operating mode for a 1.5 T MRI scanner and select operating parameters of a second exposure operating mode for a 3.0 T MRI scanner. The selected exposure operating mode may include at least one operating parameter that is specifically tailored for exposure to a particular type of MRI scanner. Processor 60 configures IMD 32 to operate in the selected exposure operating mode corresponding to the type of MRI scanner (126).

Figure 8:
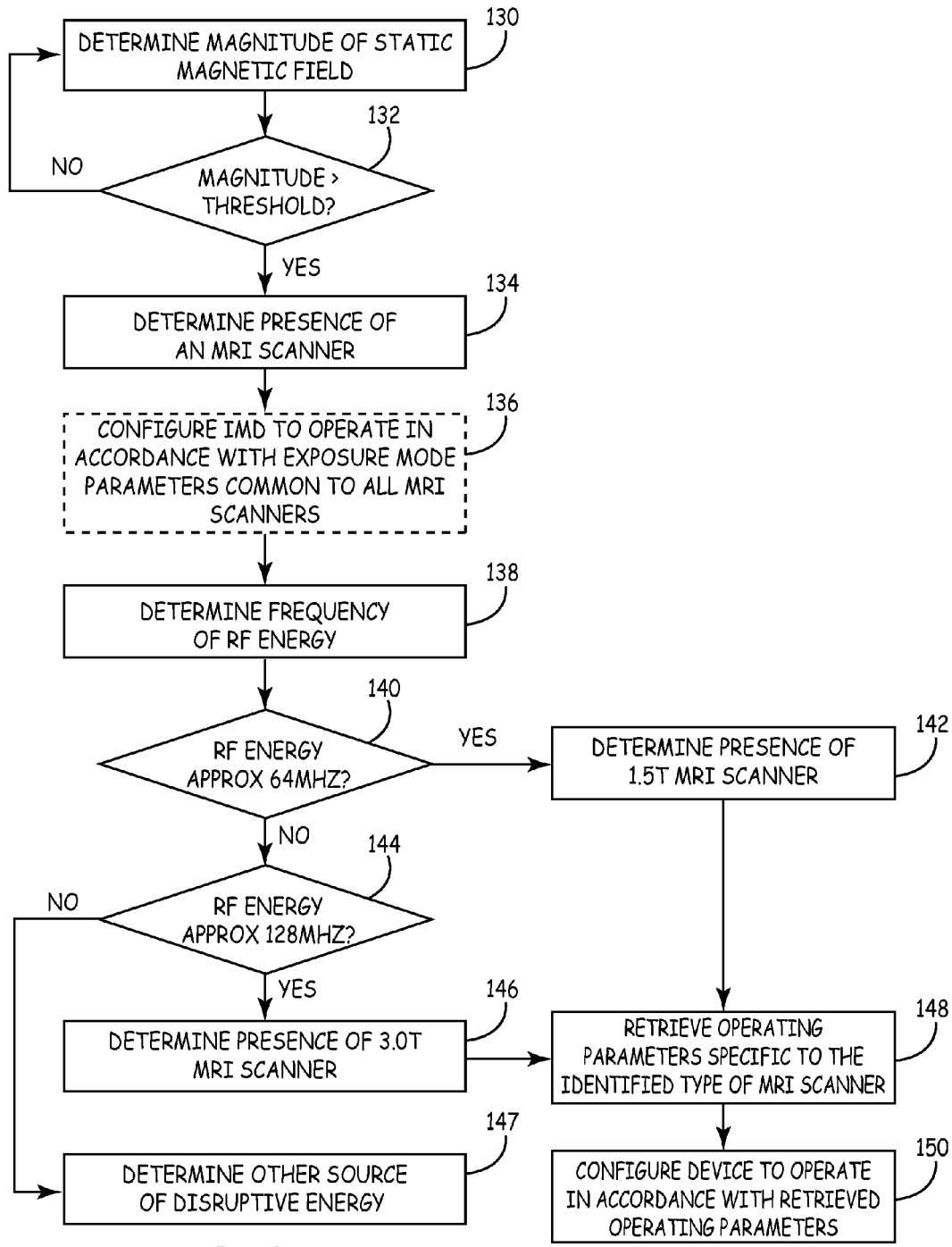
FIG. 8 is a flow diagram illustrating another example operation of an IMD detecting the presence of an MRI scanner and determining the type of MRI scanner.

FIG. 8 is a flow diagram illustrating another example operation of an IMD, such as IMD 32 or IMD 14, detecting the presence of an MRI scanner and determining the type of MRI scanner. MRI presence detection module 81 of processor 60 determines a magnitude of a static magnetic field to which IMD 32 is exposed (130). MRI presence detection module 81 may, for example, obtain a signal from magnetic field sensor 88, which may vary as a function of the magnitude of the magnetic field, and analyze the signal to determine the magnitude of the magnetic field.

MRI presence detection module 81 determines whether the magnitude of the static magnetic field is greater than a threshold (132). The threshold may be a value that is larger than the magnetic field required to enter the device into the magnet mode of operation and may encompass both the magnitude of the magnetic field generated by both 1.5 T and 3.0 T MRI scanners. When the magnitude of the magnetic field is not greater than the threshold, MRI presence detection module 81 continues to determine the magnitude of the magnetic field to which IMD 32 is exposed. When the magnitude of the magnetic field is greater than the threshold, MRI presence detection module 81 detects the presence of MRI scanner 16 (134).

In some instances, processor 60 may configure IMD 32 to operate in accordance with exposure mode operating parameters common to all MRI scanners upon detecting the presence of MRI scanner 16 (136). For example, processor 60 may retrieve common exposure mode operating parameters 94 from memory 72 upon detecting the presence of an MRI scanner. In other instances, processor 60 may configure IMD 32 to operate in a default exposure operating mode upon detecting the presence of MRI scanner 16. In this manner, processor 60 may at least partially reduce the effect of any MRI scanner immediately upon exposure to the MRI scanner. Alternatively, processor 60 may not configure any exposure mode operating parameters until the type of MRI is detected.

MRI type determination module 82 of processor 60 determines a frequency of RF energy emitted subsequent to detecting the presence of MRI scanner 16 (138). To this end, MRI type determination module 82 receives signals from one or more components that receive the RF energy emitted by MRI scanner 16, such as RF sensor 86, antenna 78, lead 34 or lead 36. MRI type determination module 82 determines whether the frequency of the RF energy is approximately equal to 64 MHZ (140). When MRI type determination module 82 determines that the frequency is approximately equal to 64 MHz, MRI type determination module 82 determines the presence of a 1.5 T MRI scanner, i.e., determines the type of MRI scanner (142).

When MRI type determination module 82 determines that the frequency is not approximately equal to 64 MHz, MRI type determination module 82 determines whether the frequency of the RF energy is approximately equal to 128 MHZ (144). When MRI type determination module 82 determines that the frequency is approximately equal to 128 MHz, MRI type determination module 82 determines the presence of a 3.0 T MRI scanner, i.e., determines the type of MRI scanner (146). When MRI type determination module 82 determines that the frequency is not approximately equal to 128 MHz, MRI type determination module 82 determines that the disruptive energy field is from a different source (e.g., a non-MRI source or a different type of MRI scanner) (147).

In response to detecting the type of MRI scanner, exposure mode selection module 84 of processor 60 selects an exposure operating mode corresponding to the type of MRI scanner (148). For example, processor 60 may select operating parameters of a first exposure operating mode for a 1.5 T MRI scanner and select operating parameters of a second exposure operating mode for a 3.0 T MRI scanner. The selected exposure operating mode may include at least one operating parameter that is specifically tailored for exposure to a particular type of MRI scanner. Processor 60 configures IMD 32 to operate in the selected exposure operating mode corresponding to the type of MRI scanner (150).

Figure 9:
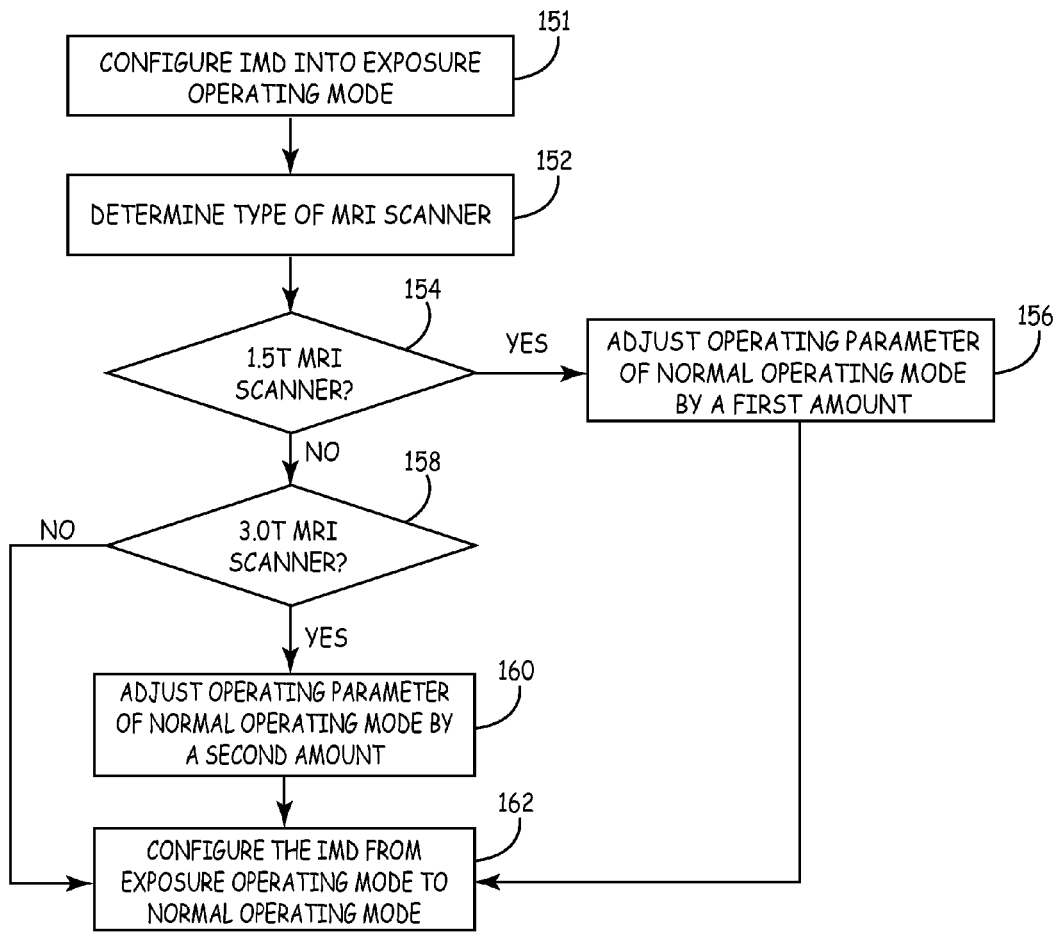
FIG. 9 is a flow diagram illustrating an example operation of an IMD adjusting one or more parameters of a normal operating mode based on the type of MRI scanner.

FIG. 9 is a flow diagram illustrating an example operation of an IMD, such as IMD 32 or IMD 14, adjusting one or more parameters that will be used when IMD 32 returns to the normal operating mode based on the type of MRI scanner. Processor 60 configures IMD 32 into an exposure operating mode prior to or upon exposure to disruptive energy field 11 (151). Processor 60 may automatically enable the exposure operating mode, e.g., in response to detecting one or more conditions, or manually enable the exposure operating mode of IMD 32, e.g., via interaction with programming device 18.

IMD 32 detects a type of MRI scanner to which IMD 32 is exposed (152). IMD 32 may, for example, detect the type of MRI scanner using the techniques described above with respect to FIG. 7 and FIG. 8. If IMD 32 determines the detected type of MRI scanner is a first type, e.g., a 1.5 T MRI scanner ("YES" branch of block 154), IMD 32 may adjust a parameter of the normal operating mode by a first amount (156). If IMD 32 determines the detected type of MRI scanner to not be the first type of MRI scanner ("NO" branch of block 154), IMD 32 determines whether the detected type of MRI scanner is a second type of MRI scanner, e.g., a 3.0 T MRI scanner (158). If IMD 32 determines the detected type of MRI scanner is the second type, e.g., a 3.0 T MRI scanner ("YES" branch of block 158), IMD 32 may adjust the parameter of the normal operating mode by a second amount (160). The second amount may be larger or smaller than the first amount. In another aspect, the first or second amount may be equal to zero such that the parameter is unchanged when exposed to one type of MRI scanner and adjusted when exposed to another type of MRI scanner.

The parameter of the normal operating mode may be, for example, a pacing amplitude, a pacing pulse width, a sensitivity of a sense amplifier or other parameter that may need to be changed due to the exposure of IMD 32 to MRI scanner 16. IMD 32 may, in some instances, not adjust any parameters of the normal operating mode based on the determination of the type of MRI scanner.

Processor 60 configures IMD 32 from the exposure operating mode to the normal operating mode after completion of the MRI scan (162). Processor 60 may automatically configure IMD 32 from the exposure operating mode to the normal operating mode or manually configure IMD 32 from the exposure operating mode to the normal operating mode via interaction with programming device 18.

Although the techniques of this disclosure are described in the context of detecting whether the MRI scanner is 1.5 T MRI scanner or a 3.0 T MRI scanner, the techniques may be applied to distinguish among other types of MRI scanners. Moreover, the techniques may be further applied to distinguish between different types of other devices that generate interfering signals, such as CT devices, electrocautery devices, diathermy devices, or the like.

The techniques described in this disclosure, including those attributed to IMD 14 and/or 32, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
    a memory to store operating parameters for a plurality of exposure operating modes, wherein the plurality of exposure operating modes includes a default exposure operating mode and at least one operating mode that corresponds to a particular type of magnetic resonance imaging (MRI) scanner; and
    a processor configured to detect a condition indicative of a presence of an MRI scanner, configure the implantable medical device to operate in accordance with operating parameters of the default exposure operating mode stored in the memory in response to detecting the presence of the MRI scanner, subsequently determine a type of MRI scanner in response to detecting the condition, retrieve from the memory the operating parameters of the one of the plurality of exposure operating modes corresponding to the determined type of MRI scanner, and configure the implantable medical device to operate in accordance with the retrieved operating parameters.

2. The device of claim 1, wherein the processor includes an MRI detection module that detects the condition indicative of the presence of the MRI scanner upon detecting at least one of a static magnetic field that exceeds a static field strength threshold, a gradient magnetic field that exceeds a gradient field strength threshold and a radio frequency (RF) signal of a particular frequency.

3. The device of claim 2, further comprising a magnetic field sensor that outputs a signal that varies as a function of the magnitude of a magnetic field, wherein the MRI detection module analyzes the signal output by the magnetic field sensor to detect the condition indicative of the presence of the MRI scanner.

4. The device of claim 3, wherein the processor includes an MRI type determination module that analyzes the output of the magnetic field sensor to detect the type of the MRI scanner to which the implantable medical device is exposed.

5. The device of claim 1 wherein the detected condition comprises a first condition, and the processor detects a second condition and determines the type of MRI scanner based on the second detected condition.

6. The device of claim 5, wherein the processor determines a frequency of RF energy to which the implantable medical device is exposed and determines the type of MRI scanner based on the frequency of the RF energy.

7. The device of claim 6, further comprising at least one of an RF sensor, an antenna and a conductor of a lead on which a signal is induced by RF energy emitted by the MRI scanner, wherein the processor analyzes the induced signal to determine a frequency of RF energy to which the implantable medical device is exposed.

8. The device of claim 1, further comprising one or more filters that are connected to respective conductors of one or more leads extending from the implantable medical device, wherein the processor configures the one or more filters to attenuate a frequency associated with the determined type of MRI scanner.

9. The device of claim 1, further comprising a magnetic field strength sensor and a radio frequency (RF) sensor, wherein the processor is configured detect a condition indicative of the presence of the MRI scanner and configure the implantable medical device to operate in accordance with operating parameters of the default exposure operating in response to the magnetic field strength sensor detecting a magnetic field having a strength that is greater than or equal to a threshold strength, and subsequently determine the type of MRI scanner and configure the implantable medical device to operate in accordance with the operating parameters of the one of the plurality of exposure operating modes corresponding to the determined type of MRI scanner based on the output of the RF sensor.

10. A method comprising:
    detecting, with an implantable medical device, a condition indicative of a presence of a magnetic resonance imaging (MRI) scanner;
    configuring the implantable medical device to operate in accordance with operating parameters of a default exposure operating mode stored in the memory in response to detecting the presence of the MRI scanner;
    subsequently, determining, with the implantable medical device, a type of the MRI scanner;
    selecting, with the implantable medical device and based on the determination, a second exposure operating mode that corresponds to operating parameters for use during exposure to a particular type of MRI scanner; and
    configuring the implantable medical device to operate in accordance with the operating parameters of the selected exposure operating mode.

11. The method of claim 10, wherein detecting the condition indicative of the presence of the MRI scanner comprises one of detecting a static magnetic field that exceeds a static field strength threshold, detecting one or more gradient magnetic fields that exceed a gradient field strength threshold and detecting one or more radio frequency (RF) signals of a particular frequency.

12. The method of claim 10, wherein determining the type of MRI scanner comprises determining the type of MRI scanner based on the detected condition.

13. The method of claim 12, wherein
    detecting the condition comprises detecting the condition based on a magnitude of a magnetic field to which the implantable medical device is exposed; and
    determining the type of MRI scanner comprises determining the type of MRI scanner based on the magnitude of the magnetic field to which the implantable medical device is exposed.

14. The method of claim 10, wherein the detected condition comprises a first condition, the method further comprising:
    detecting a second condition; and
    determining the type of MRI scanner based on the second detected condition.

15. The method of claim 14, wherein detecting the second condition comprises:
    determining a frequency of RF energy to which the implantable medical device is exposed; and
    determining the type of MRI scanner based on the determined frequency of the RF energy.

16. The method of claim 10, wherein configuring the implantable medical device to operate in accordance with the operating parameters of the selected exposure operating mode comprises configuring a filter to attenuate a frequency associated with the determined type of MRI scanner.

17. The method of claim 10, wherein:
detecting the condition indicative of the presence of the MRI scanner comprises detecting the condition indicative of the presence of the MRI scanner in response to detecting a magnetic field having a strength that is greater than or equal to a threshold strength; and
subsequently determining the type of the MRI scanner comprises determining the type of the MRI scanner based on a frequency of detected RF energy.

18. The method of claim 10, wherein the default exposure operating mode is an exposure operating mode corresponding to a first type of MRI scanner and the second exposure operating corresponds to a second type of MRI scanner different than the first MRI scanner.

19. The method of claim 18, wherein the first type of MRI scanner is a 1.5 Tesla MRI scanner and the second type of MRI scanner is a 3.0 Tesla MRI scanner.

20. An implantable medical device comprising:
means for storing a plurality of exposure operating modes, wherein each of the plurality of exposure operating modes corresponds to pacing parameters for use during exposure to a particular type of MRI scanner;
means for detecting a condition indicative of a presence of a magnetic resonance imaging (MRI) scanner;
means for determining a type of MRI scanner in response to detecting the condition;
means for selecting one of the plurality of exposure operating modes based on the determination of the type of MRI scanner; and
means for configuring the implantable medical device to operate in accordance with the operating parameters of the selected exposure operating mode.

21. The device of claim 20, wherein the detecting means detect the condition indicative of the presence of the MRI scanner in response to one of detecting a static magnetic field that exceeds a static field strength threshold, detecting one or more gradient magnetic fields that exceed a gradient field strength threshold and detecting one or more radio frequency (RF) signals of a particular frequency.

22. The device of claim 20, wherein the determining means determine the type of MRI scanner comprises determining the type of MRI scanner based on the detected condition.

23. The device of claim 22, wherein
the detecting means detect the condition based on a magnitude of a magnetic field to which the implantable medical device is exposed; and
the determining means determine the type of MRI scanner based on the magnitude of the magnetic field to which the implantable medical device is exposed.

24. The device of claim 20, wherein the detected condition comprises a first condition, the device further comprising:
means for detecting a second condition; and
wherein the determining means determine the type of MRI scanner based on the second detected condition.

25. The device of claim 24, wherein the determining means determines a frequency of RF energy to which the implantable medical device is exposed and determines the type of MRI scanner based on the determined frequency of the RF energy.

26. The device of claim 20, wherein the configuring means configures a filter to attenuate a frequency associated with the determined type of MRI scanner.

27. The device of claim 20, wherein the configuring means configures the implantable medical device to operate in accordance with a default exposure operating mode in response to detecting the presence of the MRI scanner and configures the implantable medical device to operate in accordance with the operating parameters corresponding to the particular type of MRI scanner in response to detecting the type of MRI scanner.

28. The device of claim 20, wherein the pacing parameters include at least one of a pacing amplitude, pacing pulse width, pacing mode, and pacing rate.

* * * * *